US012226625B2

(12) United States Patent
Medema et al.

(10) Patent No.: US 12,226,625 B2
(45) Date of Patent: Feb. 18, 2025

(54) WEARABLE CARDIAC DEFIBRILLATOR SYSTEMS AND METHODS AND SOFTWARE FOR CONTACTING NON-WITNESSING RESPONDERS

(71) Applicant: WEST AFFUM HOLDINGS DAC, Dublin (IE)

(72) Inventors: Douglas K. Medema, Everett, WA (US); Steven E. Sjoquist, Lynnwood, WA (US)

(73) Assignee: West Affum Holdings DAC, Dublin (IE)

( * ) Notice: Subject to any disclaimer, the term of this patent is extended or adjusted under 35 U.S.C. 154(b) by 109 days.

(21) Appl. No.: 17/589,553

(22) Filed: Jan. 31, 2022

(65) Prior Publication Data
US 2022/0152378 A1 May 19, 2022

Related U.S. Application Data

(63) Continuation of application No. 15/809,871, filed on Nov. 10, 2017, now Pat. No. 11,235,143.
(Continued)

(51) Int. Cl.
*A61N 1/04* (2006.01)
*A61B 5/00* (2006.01)
(Continued)

(52) U.S. Cl.
CPC ............ *A61N 1/046* (2013.01); *A61B 5/0006* (2013.01); *A61B 5/0022* (2013.01);
(Continued)

(58) Field of Classification Search
CPC .. A61N 1/046; A61N 1/0484; A61N 1/37258; A61N 1/3987; A61B 5/0205
See application file for complete search history.

(56) References Cited

U.S. PATENT DOCUMENTS 3,724,355 A 4/1973 Busch et al.
3,724,455 A 4/1973 Unger
(Continued)

FOREIGN PATENT DOCUMENTS

CN 101184525 A 5/2008
CN 101631589 A 1/2010
(Continued)

OTHER PUBLICATIONS

Heartstart MRx and XL AED Algorithm—Application Note, Jul. 2001, Edition 2 Philips Healthcare, USA.
(Continued)

*Primary Examiner* — Joseph M Dietrich
(74) *Attorney, Agent, or Firm* — Polsinelli PC

(57) ABSTRACT

A WCD system is configured to detect when a therapy administered to a patient by the WCD system is unsuccessful, and in response determine whether to send notifications to remote non-witness responders. The WCD system may be configured to decide to send such notifications after the WCD system determines it has administered a predetermined number of unsuccessful shocks to the patient. The predetermined number of unsuccessful shocks may be the maximum number of unsuccessful shocks the WCD system will administer to a patient, or every Xth shock (e.g., $3^{rd}$ shock). The WCD system can be configured to periodically resend the notification. The notifications may be in the form of SMS, voice messages, emails, app notifications, etc. sent to cell phones, smartphones, computers, laptops, tablets, etc. of the responders either directly, via a server, or via a CAD-coupled server.

8 Claims, 16 Drawing Sheets

SAMPLE COMPONENTS OF WEARABLE
CARDIOVERTER DEFIBRILLATOR (WCD)
SYSTEM

Related U.S. Application Data

(60) Provisional application No. 62/454,620, filed on Feb. 3, 2017.

(51) Int. Cl.

| | | |
|---|---|---|
| *A61N 1/372* | (2006.01) | |
| *A61N 1/39* | (2006.01) | |
| *G16H 20/30* | (2018.01) | |
| *G16H 40/63* | (2018.01) | |
| *G16H 40/67* | (2018.01) | |
| *G16H 50/30* | (2018.01) | |
| *G16H 80/00* | (2018.01) | |
| *H04W 4/02* | (2018.01) | |
| *A61B 5/0205* | (2006.01) | |
| *A61B 5/361* | (2021.01) | |
| *H04W 4/14* | (2009.01) | |
| *H04W 4/90* | (2018.01) | |

(52) U.S. Cl.
CPC ....... *A61N 1/0484* (2013.01); *A61N 1/37258* (2013.01); *A61N 1/3925* (2013.01); *A61N 1/3987* (2013.01); *G16H 20/30* (2018.01); *G16H 40/63* (2018.01); *G16H 40/67* (2018.01); *G16H 50/30* (2018.01); *G16H 80/00* (2018.01); *H04W 4/02* (2013.01); *A61B 5/0205* (2013.01); *A61B 5/361* (2021.01); *A61B 5/6805* (2013.01); *A61B 5/7405* (2013.01); *A61N 1/0496* (2013.01); *A61N 1/3904* (2017.08); *A61N 1/3937* (2013.01); *A61N 1/3968* (2013.01); *A61N 1/3993* (2013.01); *H04W 4/14* (2013.01); *H04W 4/90* (2018.02)

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov et al. |
| 7,120,488 B2 | 10/2006 | Nova et al. |
| 7,212,850 B2 | 5/2007 | Prystowsky et al. |
| 7,463,922 B1 | 12/2008 | Snyder et al. |
| 7,559,902 B2 | 7/2009 | Ting et al. |
| 7,587,237 B2 | 9/2009 | Korzinov et al. |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky et al. |
| 7,941,207 B2 | 5/2011 | Korzinov |
| 7,974,689 B2 | 7/2011 | Volpe et al. |
| 8,024,037 B2 | 9/2011 | Kumar |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,339,663 B2 | 5/2016 | Sullivan et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1* | 12/2008 | Volpe ............... A61B 5/0205 607/6 |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |

(56) References Cited

U.S. PATENT DOCUMENTS

| | | |
|---|---|---|
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0197324 A1 | 8/2012 | Nova |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0282072 A1 | 10/2013 | Abdeen et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0043149 A1 | 2/2014 | Cowan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039040 A1 | 2/2015 | Cowan et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2015/0352367 A1 | 12/2015 | Quan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0148495 A1 | 5/2016 | Buchanan |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0055442 A1 | 3/2018 | Freeman |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |

FOREIGN PATENT DOCUMENTS

| | | |
|---|---|---|
| CN | 102573990 A | 7/2012 |
| CN | 103354756 A | 10/2013 |
| DE | 2005060985 A2 | 6/2007 |
| EP | 2305110 A1 | 4/2011 |
| JP | 4320257 A | 3/2005 |
| JP | 2005-319306 A | 11/2005 |
| JP | 2013-511222 A | 3/2013 |
| JP | 5963767 A | 1/2014 |
| JP | 2014526282 A | 10/2014 |
| JP | 2016-209603 A | 12/2016 |
| WO | 98/39061 A2 | 9/1998 |
| WO | 1998039061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |
| WO | 2016-154425 A1 | 9/2016 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

European Search Report dated Feb. 23, 2018 for Appln. 17194049.7-1124 for West Affum Holdings Corp.

European Search Report dated Mar. 9, 2018 for Appln 18152890.2-1124 for West Affum Holdings Corp.

International Search Report 2016/154425 A1 dated Sep. 29, 2016 for Appln. PCT/US2-16/023992.

Japanese Office Action mailed Dec. 12, 2018 issued in Japanese Application No. 2018-016636 filed Feb. 1, 2018, 11 pages.

First Office Action mailed Mar. 30, 2021 in corresponding Chinese Patent Application No. 201810085761 X, filed Jan. 29, 2018, 18 pages.

\* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

SAMPLE COMPONENTS OF A WCD SYSTEM
WITH NON-WITNESS COMMUNICATION

GENERAL COMMUNICATION ARRANGEMENT

EXAMPLE RECIPIENT DEVICE WITH APP ARRANGEMENT

FIG. 8    *EXAMPLE CAD-COUPLED SERVER ARRANGEMENT (e.g. PULSEPOINT)*

WEARABLE CARDIAC DEFIBRILLATOR SYSTEMS AND METHODS AND SOFTWARE FOR CONTACTING NON-WITNESSING RESPONDERS

CROSS REFERENCE TO RELATED PATENT APPLICATIONS

This patent application is a continuation of U.S. application Ser. No. 15/809,871, filed Nov. 10, 2017, now U.S. Pat. No. 11,235,143, issued on Feb. 1, 2022, entitled "WEARABLE CARDIAC DEFIBRILLATOR SYSTEMS & METHODS & SOFTWARE FOR CONTACTING NON-WITNESSING RESPONDERS," which claims priority from U.S. Provisional Patent Application No. 62/454,620, filed Feb. 3, 2017, entitled "WEARABLE CARDIAC DEFIBRILLATOR SYSTEMS & METHODS & SOFTWARE FOR CONTACTING NON-WITNESSING RESPONDERS," the disclosures of which are hereby incorporated by reference for all purposes. The present application may also be related to U.S. application Ser. No. 14/529,082, filed Oct. 30, 2014, now U.S. Pat. No. 9,339,663, issued on May 17, 2016, entitled "WEARABLE CARDIAC DEFIBRILLATOR SYSTEM EMITTING CPR PROMPTS."

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include individuals who have had a heart attack, or a prior SCA episode. A frequent recommendation is for these people to receive an Implantable Cardioverter Defibrillator ("ICD"). The ICD is surgically implanted in the chest, and continuously monitors the person's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardioverter defibrillator ("WCD") system. A WCD system typically includes a harness, vest, or other garment for wearing by the patient. The system includes a defibrillator and external electrodes, which are attached on the inside of the harness, vest, or other garment. When a patient wears a WCD system, the external electrodes may then make good electrical contact with the patient's skin, and therefore can help monitor the patient's ECG. If a shockable heart arrhythmia is detected, then the defibrillator of the WCD system delivers the appropriate electric shock through the patient's body, and thus through the heart.

BRIEF SUMMARY

In accordance with aspects of this disclosure, a WCD system is configured to detect when a therapy administered to a patient by the WCD system is unsuccessful, and in response determine whether to send notifications to remote or non-witness responders. In some embodiments, the WCD system is configured to make a determination to send such notifications after the WCD system determines it has administered a predetermined number of unsuccessful shocks to the patient. In some embodiments, the predetermined number of unsuccessful shocks is the maximum number of shocks the WCD system will administer to a patient. In other embodiments, the predetermined number of unsuccessful shocks is every Xth shock (for example, every $2^{nd}$ or $3^{rd}$ shock). In some embodiments, the WCD system can be configured to periodically resend the notification.

In some embodiments, the WCD system transmits the notifications as SMS message to cell phone or smartphones of the responders. In other embodiments, the WCD system may make telephone calls to the responders in which the notifications may be in the form of recorded or synthesized voice messages. In yet other embodiments, the WCD system may send information to a WCD system server, which in turn sends SMS and/or voice messages to the responders, or emails or application notifications that the responders receive via email or notification apps running on their computers, smartphones, laptops or other "connected" devices. In still other embodiments, the WCD system may send information to a computer-aided dispatch (CAD)-coupled server (for example, a PulsePoint server) which then sends notifications to any of its users that are near the patient's location.

The foregoing brief summary is illustrative only and is not intended to be in any way limiting. In addition to the illustrative aspects, embodiments, and features described above, which need not all be present in all embodiments of the inventions disclosed herein, further aspects, embodiments, and features are set forth in the drawings and the following detailed description.

DETAILED DESCRIPTION

A wearable cardioverter defibrillator (WCD) system made according to embodiments has several components. These components can be provided separately as modules that can be interconnected, or can be combined with other components, etc.

Figure 1:
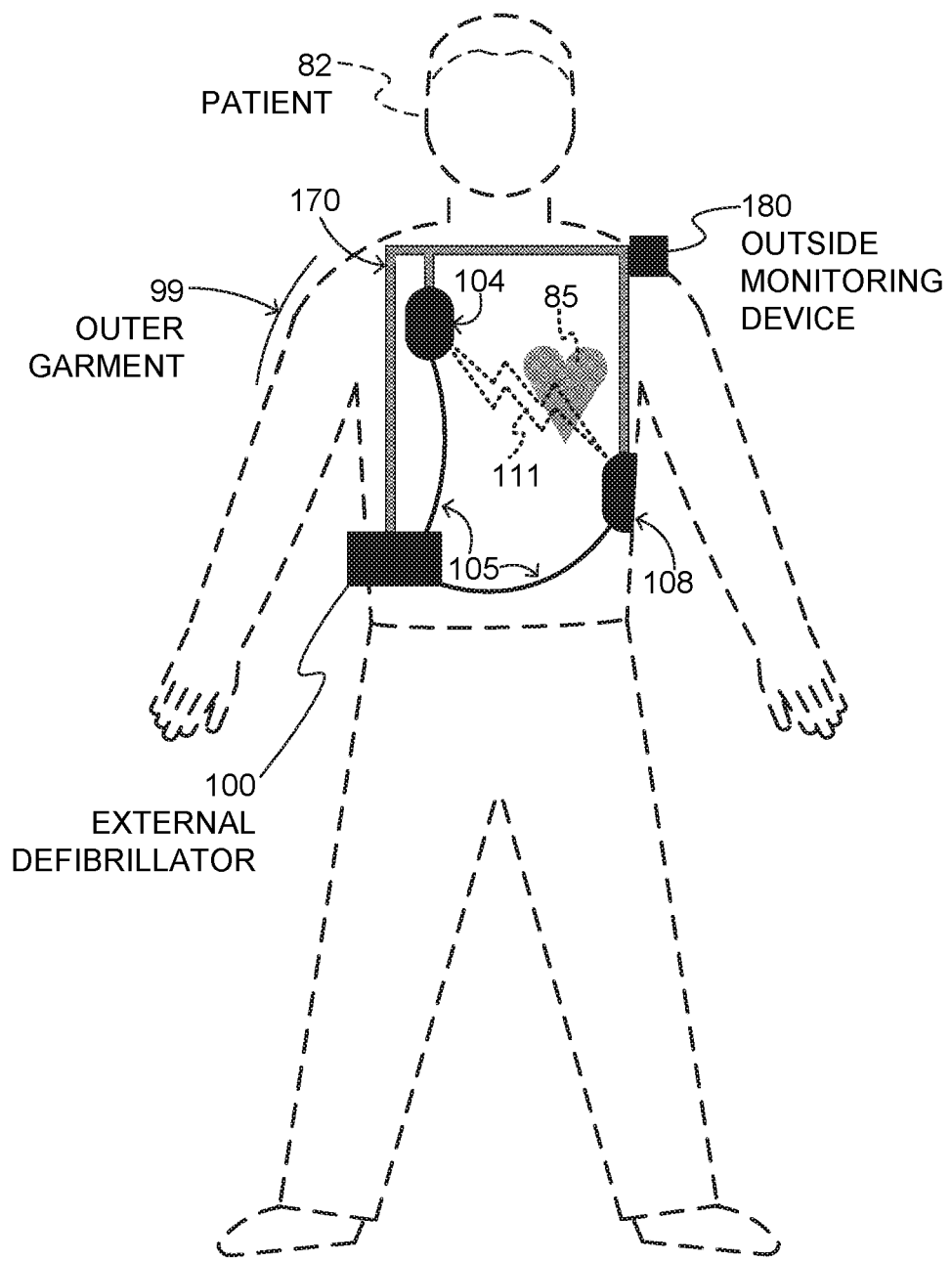
FIG. 1 is a diagram of components of a sample wearable cardioverter defibrillator (WCD) system, made according to embodiments.

FIG. 1 depicts a patient 82. Patient 82 may also be referred to as a person and/or wearer, since that patient wears components of the WCD system.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways in different embodiments. For example, in one embodiment implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US 2017/0056682 A1, which is incorporated herein by reference. After review of this disclosure, in such embodiments, the person skilled in the art will recognize that additional components of the WCD system can be in the housing of a support structure instead of attached externally to the support structure, for example as described in the 2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as shock, defibrillation shock, therapy or therapy shock, is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, some embodiments of external defibrillator 100 can initiate defibrillation (or hold-off defibrillation) based on a variety of inputs, with ECG merely being one of them.

Accordingly, in some embodiments of external defibrillator 100, signals such as physiological signals containing physiological data are obtained from patient 82. While the patient may be considered also a "user" of the WCD system, in some embodiments, for example, a user of the WCD may be a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
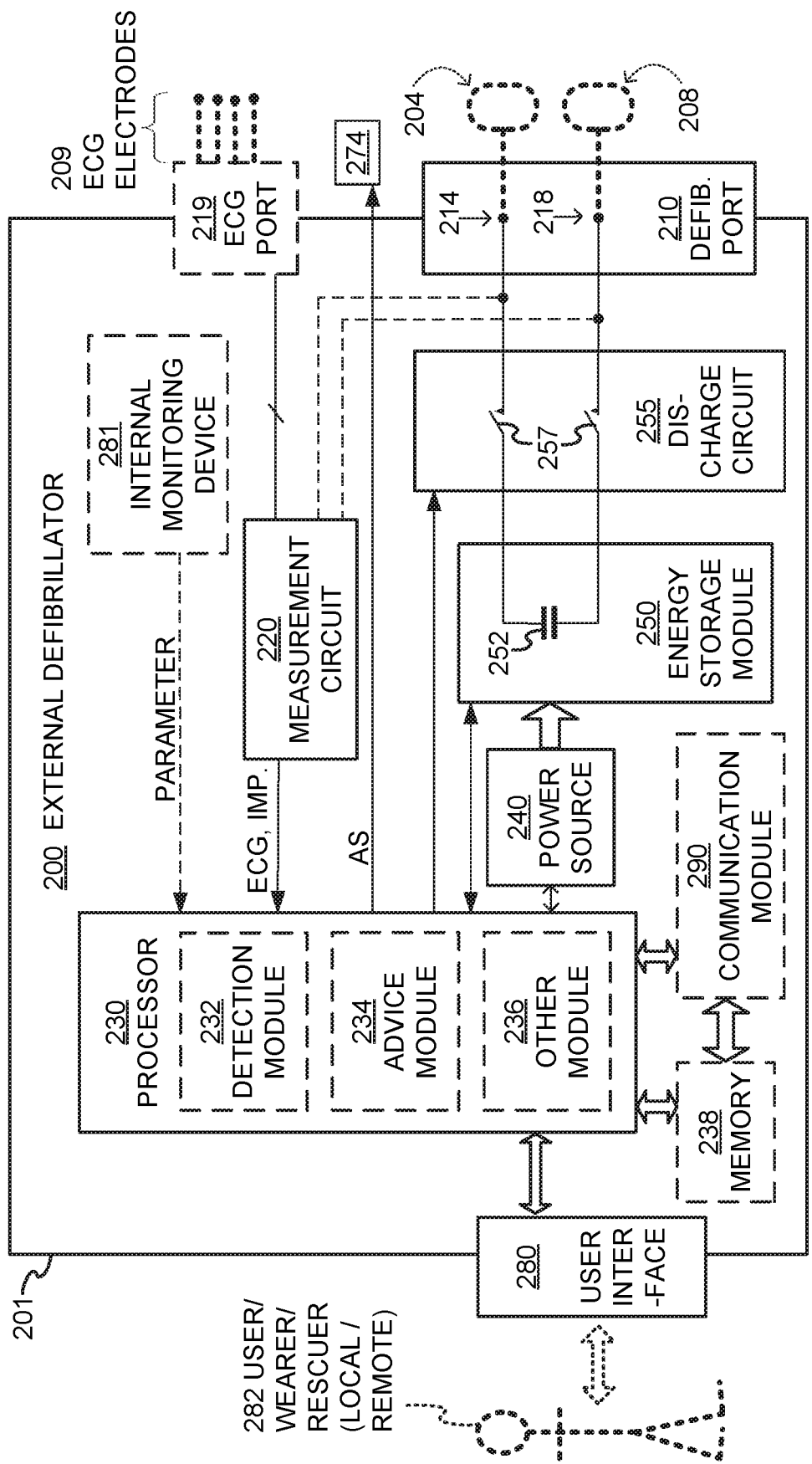
FIG. 2 is a diagram showing sample components of an external defibrillator, such as the one belonging in the WCD system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or user 282 can be a local rescuer at the scene, such as a bystander who might offer assistance, or a trained person.

Or, user 282 might be a remotely located trained caregiver in communication with the WCD system.

User interface 280 can be made in many ways according to various embodiments. User interface 280 may include output devices, which can be visual, audible or tactile, for communicating to a user by outputting images, sounds or vibrations. Images, sounds, vibrations, and anything that can be perceived by user 282 can also be called human perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which monitoring device can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an SpO2 sensor, and so on. It will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2 or CO2; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, one of the transducers may include a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 are types of transducers that can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally, a WCD system according to embodiments also includes a fluid that it can deploy automatically between the electrodes and the patient's skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from processor 230 that is described more fully later in this document.

In some embodiments, defibrillator 200 also includes a measurement circuit 220, as one or more of its sensors or transducers. Measurement circuit 220 senses one or more electrical physiological signals of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the physiological input reflects an ECG measurement. The parameter can be an ECG, which can be sensed as a voltage difference between electrodes 204, 208. In addition the parameter can be an impedance, which can be sensed between electrodes 204, 208 and/or the connections of ECG port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module implemented using software includes a set of the instructions so as to offer or fulfill a particular functionality. Embodiments of modules and the functionality delivered are not limited by the embodiments described in this document.

Processor 230 can be considered to have one or more modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Various embodiments of processor 230 can include additional modules, such as other module 236, for other functions. In addition, if internal monitoring device 281 is indeed provided, it may be operated in part by processor 230, etc.

Embodiments of defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. Module 290 may also include such sub-components as may be deemed necessary by a person skilled in the art, for example an antenna, portions of a processor, supporting electronics, outlet for a telephone or a network cable, etc. This way, data, commands, etc. can be communicated. The data can include patient data, event information, therapy attempted, CPR performance, system data, environmental data, and so on. Defibrillator 200 in some embodiments can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

Figure 3:
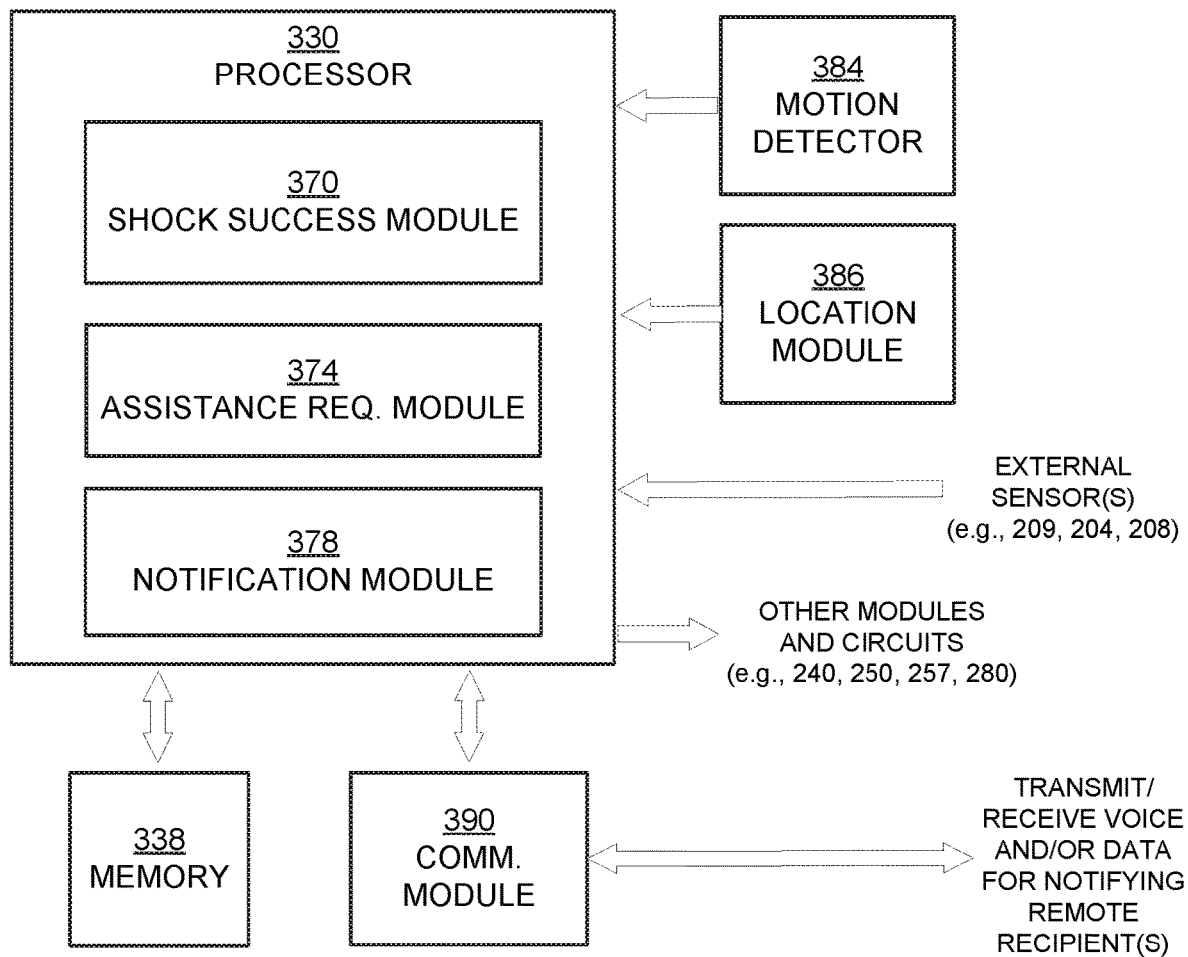
FIG. 3 is a diagram showing a collection of sample components of WCD systems for notifying remote responders, made according to embodiments.

FIG. 3 is a diagram showing sample components of an external defibrillator 301 same or similar to those of external defibrillator 200 of FIG. 2, in which some components are shown in more detail and some in less detail, according to embodiments. External defibrillator 301 can implemented in a WCD to deliver appropriate therapy (e.g., defibrillation shocks, cardioversion shocks, pacing, etc.) to a patient with an arrhythmia.

In embodiments, external defibrillator 301 includes a processor 330 coupled to a memory 338, a motion detector 384, a location module 386, and a communication module 390. Processor 330, memory 338, and communication module 390 are implemented in some embodiments as described above in conjunction with FIG. 2 for processor 230, memory 238, and communication module 290. Memory 338 can also be configured with patient ID information intended for inclusion in notifications that are described further below. External defibrillator 301, in embodiments, also includes other modules and components as shown in FIG. 2, but are omitted in FIG. 3 as they have already been described in detail in conjunction with FIG. 2.

In some embodiments, the components of external defibrillator 301 shown in FIG. 3 are disposed in a single housing or unit that is coupled to the support structure such as support structure 170 (FIG. 1). In other embodiments, one or more of these components are distributed over other parts of the WCD system. For example, in some embodiments processor 330, location module 386 and communication module are implemented at least in part using a mobile personal communication device such as a smartphone-like device as described below in conjunction with FIG. 5.

Motion detector 384, in some embodiments, is configured to detect motion of the patient, including patient motion due to having CPR performed on the patient. In embodiments, motion detector 384 is implemented using one or more of an accelerometer, force sensor, position sensor, transthoracic impedance sensors, etc. Some examples of positions sensors include UWB position sensors, and magnetic field position sensors such as used in TrueCPR™ devices available from Physio-Control, Inc., Redmond, WA).

Location module 386, in some embodiments, is configured to determine the location of the patient. In some embodiments location module 386 determines the location of external defibrillator 301, or other component of the WCD system to indicate the location of the patient. Location module 386 in some embodiments uses one or more of GPS, cellular tower location, Wi-Fi access point locations, inertial navigation, etc. to determine the location of the patient. In embodiments of the WCD system having a mobile communication device (e.g., smartphone-like device), the location module includes an API to interface with a location service such as Google Location Services.

In addition, in some embodiments processor 330 includes a shock success module 370, assistance request module 374, and a notification module 278. In some embodiments Shock success module 370, assistance module 374, and notification module 278 are implemented at least in part using software or programming stored in memory 338.

Shock success module 370 is configured to detect whether a shock provided to the patient was successful in removal of the patient's arrhythmia condition (e.g., VF or VT). In some embodiments, shock success module 370 is coupled to detection module 232 and advice module 234 to obtain information used to determine if a shock applied to the patient was successful. Responsive to shock success module 370 detecting that the shock was unsuccessful, in some embodiments external defibrillator 301 may be configured to deliver another shock to the patient. In some such embodiments, external defibrillator 301 may be configured so that it will stop delivering shocks after a preset or preconfigured number of consecutive unsuccessful shocks even if external defibrillator 301 determines another shock is indicated.

Assistance request module 374 is configured to determine whether one or more other people or parties (also referred to as responders in this context) should be notified when shock success module 370 detects that a shock delivered to the patient was unsuccessful. In some embodiments, assistance request module 374 can be configured with a threshold number of consecutive delivered unsuccessful shocks at which the other responders should be notified. For example, in some embodiment the threshold number can be set or configured by a clinician when fitting the patient with the WCD, in the factory, or set dynamically by processor 330 using logic or algorithm(s). Further, in some embodiments assistance request module 374 is configured to determine whether one or more other people or parties should be notified that the patient requires cardiopulmonary resuscitation (CPR). Stated another way, in some embodiments shock success module 370 and assistance request module 374 are configured to detect the occurrence of N (N being an integer greater than or equal to 1) unsuccessful shocks administered to the patient, and in response thereto determine that one or more responders should be notified that the patient requires further assistance that at least includes CPR. In some embodiments, N is the maximum number of unsuccessful shocks that the WCD system will administer to a patient.

In a further refinement, after a notification is sent in response to the maximum number of unsuccessful shocks, assistance request module 374 may be configured to cause the notification to be periodically resent (e.g., every 60 seconds). In some embodiments, the resending of notifications may be terminated in response to one or more responders sending a message to the WCD system that the responder(s) are in the process of responding to the notification.

In other embodiments, shock success module 370 and assistance request module 374 are configured to detect the occurrence of the Xth shock (X being an integer greater than or equal to 1) unsuccessful shocks administered to the patient, and in response thereto determine that one or more responders should be notified that the patient requires further assistance that at least includes CPR. For example, in some embodiments X is set to 2 so that a notification is sent every other unsuccessful shock. In another example embodiment, X is set to 3 so that a notification is sent every third unsuccessful shock.

In some embodiments, WCD system 301 includes a proximity detector (not shown) such as, for example, disclosed in U.S. Pat. No. 9,339,663 issued May 17, 2016 and entitled "WEARABLE CARDIAC DEFIBRILLATOR SYSTEM EMITTING CPR PROMPTS", incorporated by reference herein in its entirety. The proximity detector can be used to detect when there are bystanders near the patient. Responsive to the proximity detector detecting such a bystander, in some embodiments, assistance request module 374 is configured to make a determination that a notification is not needed to be sent to potential non-witness responders. Conversely, responsive to the proximity detector detecting that there are no nearby bystanders, in some embodiments assistance request module 374 will make a determination that a notification should be sent to non-witness responders.

In still other embodiments, when the aforementioned proximity detector detects nearby bystanders, assistance request module 374 is configured to make a determination that a notification should not be sent to non-witness responders (as described above). However, in addition, if after a preset period of time (e.g., 30 seconds) the WCD system does not detect CPR has been started on the patient, assistance request module 374 is further configured to change the determination so that it makes a determination that a notification should be sent to the non-witness responders. In some embodiments, the WCD system may detect CPR by detecting changes in the patient's transthoracic impedance.

Notification module 378, in some embodiments, is configured to obtain emergency event information, patient identification information, patient location information, and responder contact information in response to a determination by assistance request module 374 that one or more non-witness responders should be notified. In some embodiments, the emergency event information (for example, Shock Delivered, VF Detected, VT Detected, Bradycardia Detected and/or Asystole Detected) and the patient identification information is obtained from memory 338 and/or one or more modules of processor 330 such as, for example, modules 232, 234, and 236 (previously described in conjunction with FIG. 2). Notification module 378 in some embodiments is configured to obtain patient location information from location module 386 (described further below). In some embodiments, the responder contact information can be entered by the user or clinician when the patient is fitted with the WCD system and updated as desired. The responders can be people who might be expected to be near patient 182 for significant periods of time such as, for example, spouse, relatives, neighbors, co-workers, assistants, etc. so that assistance can be quickly provided to patient 182.

Communication module 390, in some embodiments, is configured to transmit at least some of the information obtained by the notification module to one or more respondents using the responder contact information. In some embodiments, communication module 390 is implemented using a wireless transceiver such as, for example, cellular voice, cellular data, SMS, "Wi-Fi", "Wi-Fi Direct", "Bluetooth", "ZigBee", etc. In some embodiments, these wireless connections may be used to communicate via a server that is configured to initiate communications to the one or more responders using SMS, email, voice (cellular and POTS), client application notifications (e.g., client apps configured on respondents' computing devices such as smartphones), etc. to the one or more responders. Various embodiments of these communications are described below in conjunction with FIGS. 4-8.

Some of the above-described embodiments of a WCD system can be advantageously used to provide notifications to one or more responders who did not witness the patient experiencing an emergency arrhythmia event so that these responders can provide assistance. For example, if the patient experienced an arrhythmia that required a shock to correct, and one or more shocks were administered but were unsuccessful, a WCD system that included embodiments of external defibrillator 301 (FIG. 3) could notify a non-witnessing responder to provide additional assistance such as CPR, and/or drug treatment (e.g., epinephrine, atropine) if the responder is a trained medical responder such as a paramedic. The notification can include information indicating the patient's location so that the responder(s) can go as quickly as possible to the patient and provide additional assistance such as CPR. In cases where the patient was alone when the arrhythmia event occurred, there may be no bystanders to provide such additional assistance and potential responders would not otherwise know of the event. Another scenario where embodiments can be advantageously can occur when the patient and friends/relatives/caregivers are in different rooms in their home or workplace, or perhaps the patient is outside of his/her home while the caregiver is inside the house (or vice versa). While WCDs typically use audible alerts to alert both the patient and caregiver, something as simple as a television being on could obscure the caregiver's hearing the alert. Such notifications provided by external defibrillator 301 can improve patient outcomes by decreasing the amount of time before the patients start receiving assistance such as CPR, compared to systems that do not provide such notifications. In some embodiments, the WCD system can determine potential responders that are near the patient's location and notify only those responders. These advantages can also be realized in some of the embodiments described below.

Figure 4:
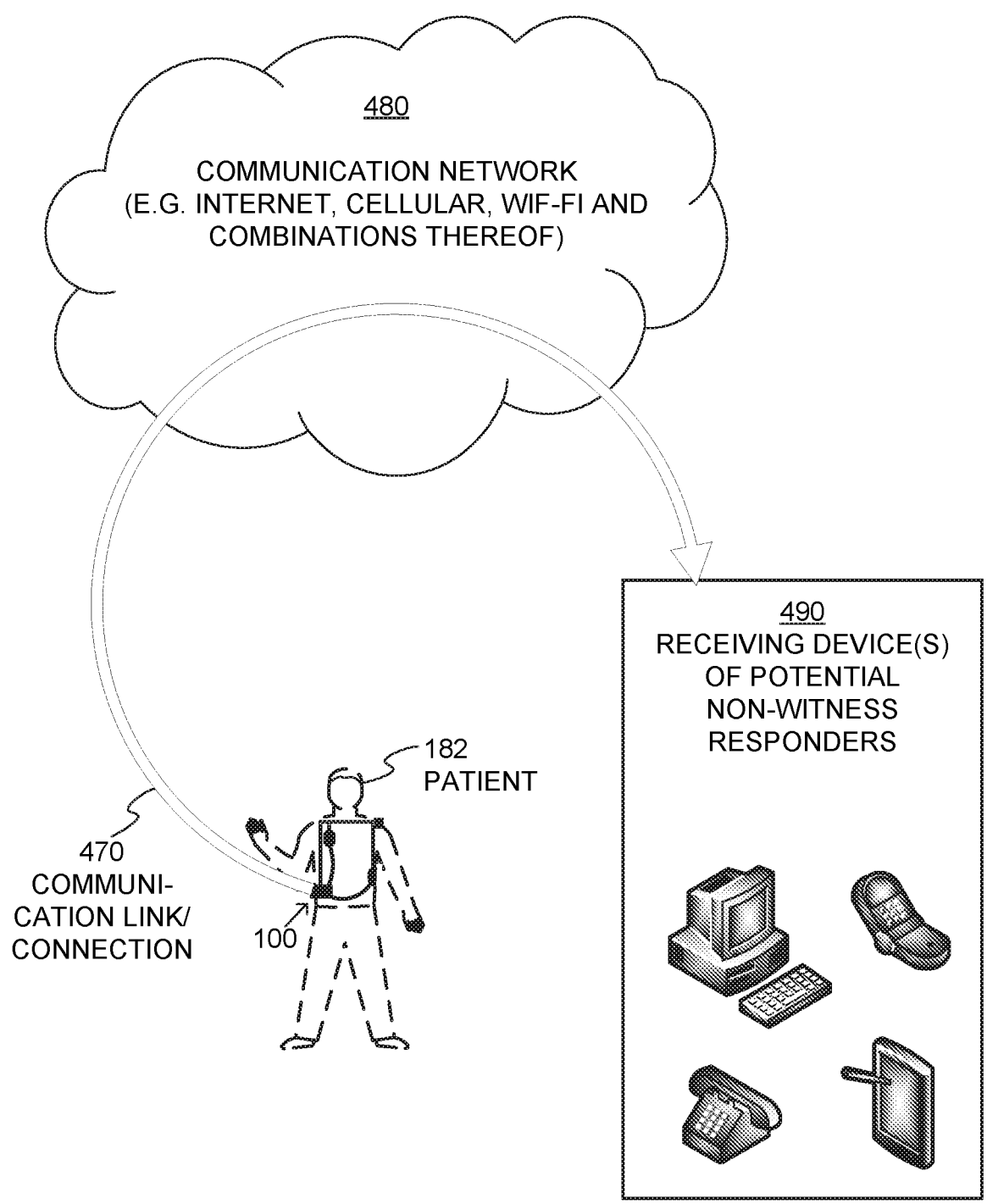
FIG. 4 is a diagram showing a general communication arrangement for a WCD system for notifying remote responders, made according to embodiments.

FIG. 4 is a diagram showing a general communication arrangement for a WCD system for notifying remote responders, made according to embodiments. FIG. 4 illustrates the general flow of a notification of unsuccessful shock(s) from the WCD system (e.g., from patient worn external defibrillator 100 described in conjunction with FIG. 1), over a communication link or connection 470, and onto remote or non-witness responders via a communication network 480 their receiving devices 490. Communication network 480 is implemented according to various embodiments using a combination of wireless and/or wired sub links that can include the Bluetooth connections, WLAN networks, Internet, POTS, cellular voice networks, cellular data networks, and/or other communication networks. The respondents' devices 490 can include, according to embodiments, computers connected to the Internet, landline telephones, cellular telephones, pagers, PDAs, and/or smartphones or connected tablets configured with notification applications, etc.

Figure 5:
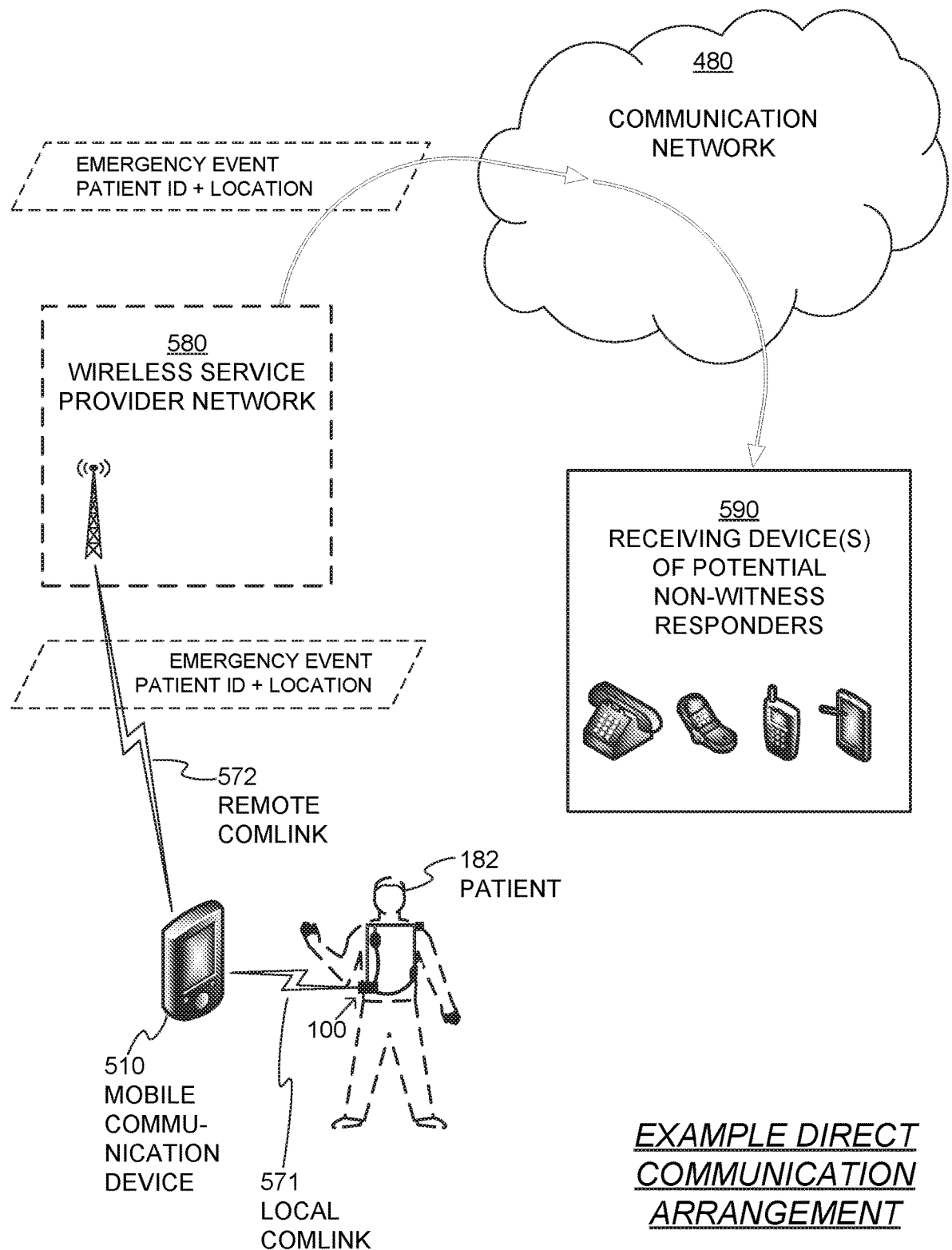
FIG. 5 is a diagram showing a communication arrangement for a WCD system having a mobile communication device for notifying remote responders, made according to embodiments.

FIG. 5 is a diagram showing an embodiment of particular communication arrangement implementing the general arrangement shown in FIG. 4. The arrangement of FIG. 5, in this embodiment, includes a mobile communication device 510 configured to communicate with external defibrillator 100 through a local commlink 571. In some embodiments, mobile communication device 510 and local commlink 571 are implemented as described in U.S. patent application Ser. No. 13/959,894 filed Aug. 6, 2013 and entitled "MOBILE COMMUNICATION DEVICE & APP FOR WEARABLE DEFIBRILLATOR SYSTEM". In embodiments, mobile communication device 510 can be a wireless telephone, a smartphone, a Personal Digital Assistant (PDA), a personal electronic device, a pager, a laptop computer, a tablet, an e-reader, and so on. Such mobile communication devices are increasingly becoming more than just wireless voice communication devices. In addition to handling voice data, some mobile communication devices are essentially portable computing devices that can support a variety of applications such as email, web browsing, text processing applications, contact applications, scheduling applications, games, and so on.

In many cases, mobile communication device 510 acts as a proxy for also the presence of patient 182. Patient 182 may carry device 510 in a pocket, in a special holder, or even wear it on their wrist. In other words, the location of patient 182 can sometimes be presumed to be the same as the location of mobile communication device 510. In embodiments, mobile communication device 510 includes a module that has location determining circuitry and/or software for determining the location of the mobile communication device using GPS, cell tower locations, Wi-Fi access point locations, inertial navigation, etc., as is currently available in modern smartphones.

The arrangement of FIG. 5 uses wireless communication links. A wireless communication link is also sometimes referred to herein as a "comlink". For purposes of this document, a "remote comlink" means a wireless communication link established between devices that are typically at least 500 feet (150 m) away from each other, and often farther, such as a cellular communication link. A "local comlink" as used in this context means a wireless communication link established between devices that are at most 50 feet (15 m) away from each other, and typically closer.

In embodiments, mobile communication device 510 can communicate with a wireless service provider network 580 via a remote comlink 572. Remote comlink 572 can be direct, or can be established between device 510 and network 580 via intermediary points, such as a Wireless Access Point, Wi-Fi, and so on; even in those cases, however, a remote comlink includes at least one leg of a wireless communication link that is at least 500 feet (150 m) long. On or more of the legs between intermediary points may include a network land line. Network 580 can be coupled with a communications network 480, which can be the Internet or one of the networks of the Internet, POTS, etc. Receiving devices 590 (of the potential non-witness responders) can be part of network 480, and in effect be cloud-based. Receiving devices 590, in embodiments, may be any one of a landline telephone, a cellular telephone, a desktop computer, a server, a mainframe computer, and so on. Accordingly, mobile communication device 510 can communicate and exchanging data with receiving devices 590 of potential remote or non-witness responders, at least according to the arrangement of FIG. 5.

In some embodiments, mobile communication device 510 and/or receiving devices 190 includes an application, also known as an "app" that facilitate the users of these devices in sending and receiving communications, including notifications.

In many embodiments, external defibrillator 100 and mobile communication device 510 are capable of establishing local comlink 571, and therefore can exchange data between them via the local comlink. Data can be exchanged in either direction, or in both directions. In some embodiments, local comlink 571 uses radio transmission technology that can be broadband and/or shortwave. Local comlink 571 may use Bluetooth technology, Wi-Fi technology, or equivalent. Local comlink 571, coupled with the abilities of mobile communication device 510, enables external defibrillator 100 to communicate better with its environment, as will be seen in more detail later in this document.

In other embodiments, instead of comlink 571, defibrillator 100 and mobile communication device 510 are capable of establishing a local link that is wired, and therefore can exchange data between them via the wired local link. The wired link can be by any suitable wired connection, for example via a USB or Lightning connection. Communication would be established by the connecting, whereupon the two devices would recognize each other, and so on.

In operation to provide a notification of unsuccessful shock(s) (as described in conjunction with FIG. 3), in some embodiments, after detection of the unsuccessful shock(s) and a determination that notifications should be sent to non-witness responder(s), external defibrillator 100 uses local comlink 571 to provide emergency event information to mobile communication device 510. In some embodiments, external defibrillator 100 also provides patient location information and/or patient ID information to mobile communication device 510. In some embodiments, external defibrillator 100 may be configured to send the emergency event information to mobile communication device 510 before or concurrently with the determination that notifications should be sent to non-witness responder(s).

Mobile communication device 510 then uses remote link 572 to provide information related to the emergency event, patient ID, and location to wireless service provider network 580. Mobile communication device 510 typically uses responder contact information stored in its memory to direct information to the devices 590 of non-witness respondents. In other embodiments, mobile communication device 510 obtains the contact information form external defibrillator 100. In some embodiments, mobile communication device 510 is configured with the patient ID information, and can obtain the location information using its own location determination functionality (as opposed to obtaining it from external defibrillator 100). In some embodiments, the notification transmitted by the mobile communication network includes information processed and/or revised from the event information obtained from external defibrillator 100 to comply with patient privacy regulations and to provide only what is needed by the potential non-witness responders to be able to quickly travel to the patient and provided assistance such as, for example, CPR.

Wireless service provider network 580, in some embodiments, then uses communication network 480 to provide the notification to the device(s) 590 of the potential non-witness responders.

Figure 6:
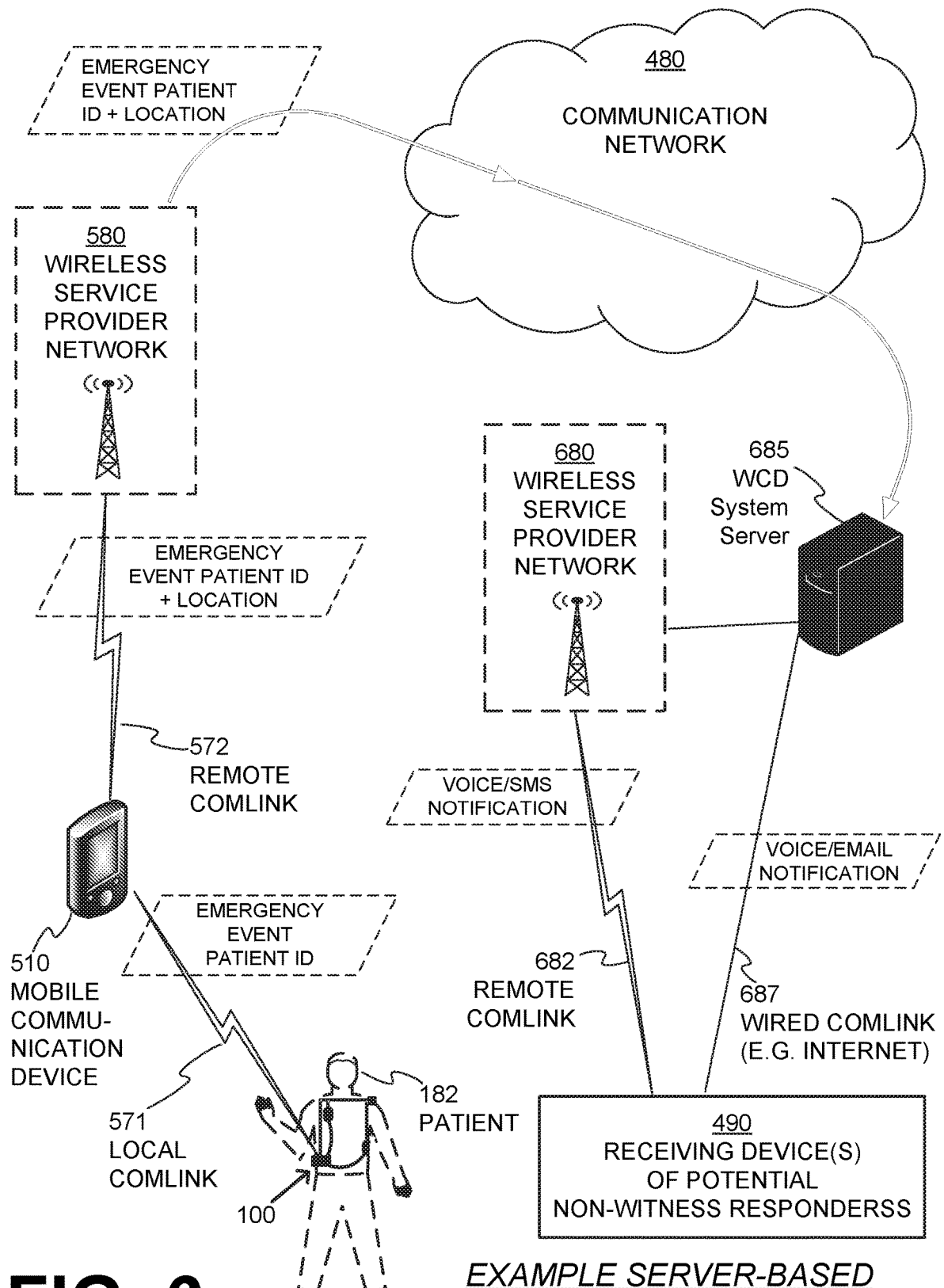
FIG. 6 is a diagram showing a communication arrangement for a WCD system having a WCD system server for notifying remote responders, made according to embodiments.

FIG. 6 is a diagram showing an embodiment of particular communication arrangement implementing the general arrangement shown in FIG. 4. The arrangement of FIG. 6, in this embodiment, is similar to the arrangement of FIG. 5 but also includes a WCD server 685 configured to communicate with receiving device(s) 490 through a wireless service provider network 680 via a remote comlink 682 and/or a wired commlink 687. These additional elements may be considered a part of communication network 480 but are "broken out" in FIG. 6 to facilitate this description.

In some embodiments of the arrangement of FIG. 6, mobile communication device 510 receives information from external defibrillator 100 via local commlink 571, sends notification information to wireless service provider network 580, which then sends notification information to communication network 480, all as described above in conjunction with FIG. 5.

For such embodiments, the notification information sent by mobile communication 510 also includes information addressing the notification to WCD server 685. In some embodiments, the recipient contact information is stored in WCD server and the WCD server is configured to access the recipient contact information based on the emergency event and/or patient ID information.

WCD server 685 then processes the notification information received via communication 480 to generate one or more notification messages. For example, in some embodiments, WCD server 685 is configured with profile and preference information for each responder and generates the appropriate notification message for that responder (and/or the responder's device 490). For receiving devices 490 that wireless (e.g., cell phones, smartphones, connected tablets, connected laptops, pagers, etc.), WCD system server 685 in some embodiments generates one or more SMS messages, recorded/synthesized voice messages and/or emails to be sent to those devices via a wireless service provider network 680 and a remote comlink 682. Similarly, for receiving devices 490 that are wired or potentially wired (e.g., a landline telephone, a desktop computer, etc.), WCD system server 685 in some embodiments generates one or more email messages, recorded or synthesized voice messages to be sent to those devices via a wired comlink 687 such as the Internet, POTS, etc. The particular type of notification message for each receiving device 490 may be selected by WCD system server 685 based on contact information, emergency event and/or stored profile/preference information.

Further, in some embodiments, in response to received notifications, a responder can use his/her receiving device 490 to send a message to WCD server system 685 indicating that the responder is going to respond to provide the additional assistance, or cannot respond, etc. Still further, in some such embodiments, the WCD system server can then send notifications to other responders indicating the responder(s) who have indicated that they were are responding to provide the additional assistance. For example, the WCD system service can send these notifications to other responders via SMS message, or in direct application communication (described below).

Figure 7:
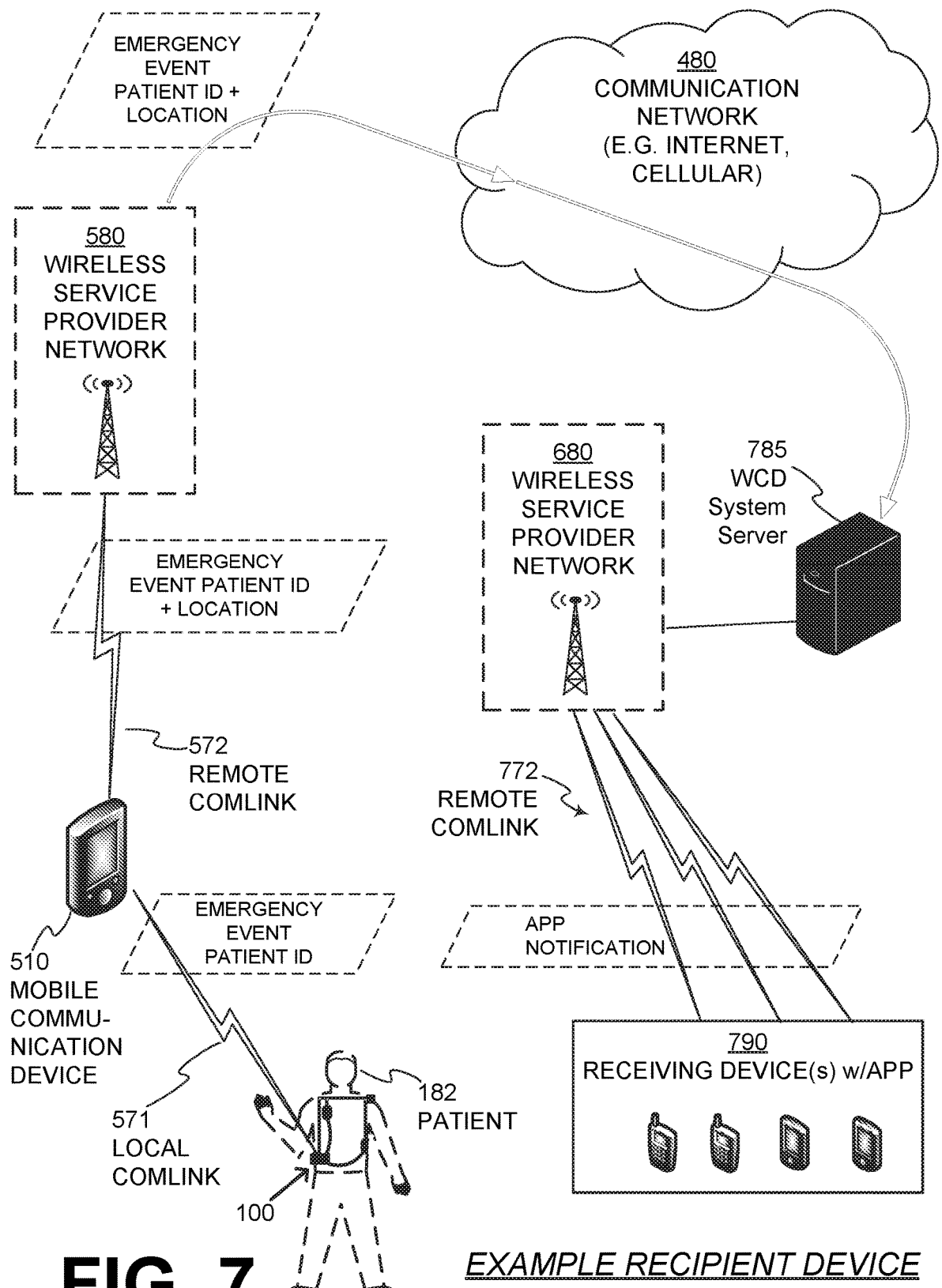
FIG. 7 is a diagram showing a communication arrangement for a WCD system for notifying remote responders having devices configured with a notification app, made according to embodiments.

FIG. 7 is a diagram showing an embodiment of particular communication arrangement implementing the general arrangement shown in FIG. 4. The arrangement of FIG. 7, in this embodiment, is similar to the arrangement of FIG. 6 but also includes receiving devices 790 of non-witness or remote responders having a notification app installed for receiving notifications from a WCD system server 785. WCD system server 785, in some embodiments has the same functionality as WCD system server 685 (FIG. 6) but in addition is configured to send notifications to the receiving devices 790. In some embodiments, WCD system server 785 and the apps installed on receiving devices 790 implement an event subscription architecture. For example, in some embodiments when WCD server 785 receives a notification of an emergency event experienced by patient 183 via communication 480, this generates an event in the WCD system server 785. In response, WCD system server 785 publishes the event to subscribed clients (i.e., the apps installed on receiving devices 790) via wireless service provider network 680 and remote commlink 772. In other embodiments, other messaging mechanisms can be used instead of or in combination with an event subscription architecture, such as for example SMS text, Apple iMessage, or other network messaging systems. In response to receiving the published event, the apps on receiving devices 790 then provide an alarm or alert via the user interface of the receiving devices. In some embodiments, the app is configured to provide the alert using audio, visual and/or vibration outputs of the receiving device.

Figure 8:
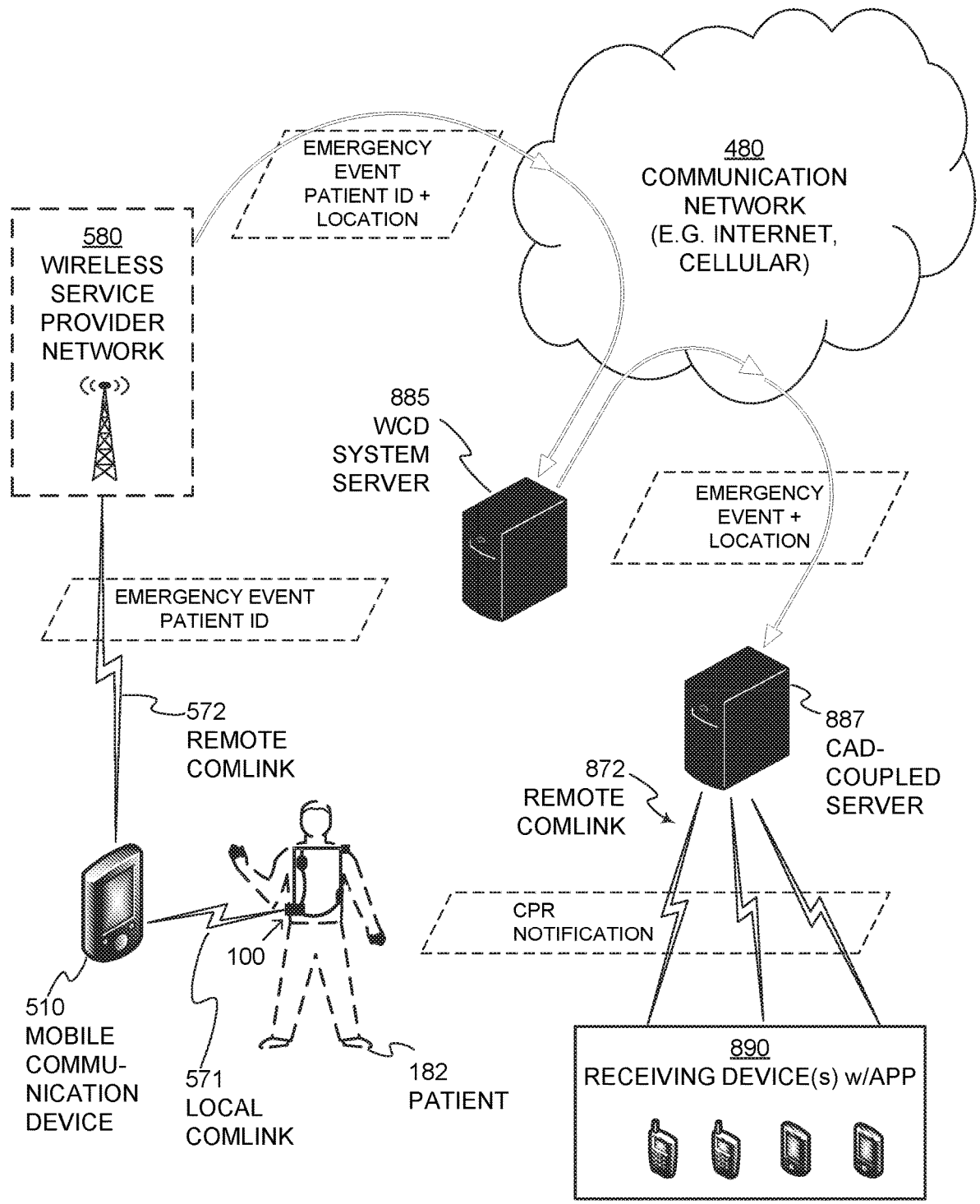
FIG. 8 is a diagram showing a communication arrangement for a WCD system having a WCD system server communicating with a CAD-coupled server for notifying remote responders, made according to embodiments

FIG. 8 is a diagram showing an embodiment of particular communication arrangement implementing the general arrangement shown in FIG. 4. The arrangement of FIG. 8, in this embodiment, is similar to the arrangements of FIGS. 6 and 7 but also includes a WCD system server 885 and a computer-aided dispatch (CAD)-coupled server 887 and receiving devices 890 having apps for use with CAD-coupled server 887. In one embodiment, CAD-coupled server 887 is implemented using a PulsePoint server, available from the PulsePoint Foundation, Pleasanton, CA (www.PulsePoint.org).

CAD-coupled server 887 is typically coupled to the CAD system (e.g., the emergency response or 911 system, not shown in FIG. 8) for a locality, and also to a plurality of subscribers' receiving devices 890 via a remote comlink 872. In a typical operation, CAD-coupled server 887 would receive notification of certain types of emergency events (e.g., cardiac arrest and the patient's reported location) from the CAD system and, in response, send an alert (e.g., "CPR needed") to subscribers' devices that are near the patient's reported location via remote comlink 872.

In accordance with embodiments, WCD system server 885 provides emergency event and location information to CAD-coupled server 887 (i.e., instead of or in addition to the notification from the CAD system). In response to this emergency event and location information, CAD-coupled server 887 is configured to provide an assistance-needed notification (e.g., a CPR needed notification in some embodiments) to the devices 990 of nearby responders who have the app installed for receiving notifications from CAD-coupled system server 887. These responders may not people who do not know patient 182, but may be "good Samaritans" who have subscribed or registered with the CAD-coupled server (e.g., PulsePoint users). WCD system server 885, in some embodiments has the same functionality as WCD system server 685 (FIG. 6) or WCD system server 785 (FIG. 7), but in addition is configured to send notifications to CAD-coupled server 887. In some embodiments, WCD system server 885 also sends notifications to non-witness responders to devices 790 (FIG. 7) as described above for WCD system server 785, and/or device 490 (FIG. 6) as described above for WCD system server 685.

The various embodiments of the devices and/or systems disclosed in this document perform functions, processes and/or methods as described above. These functions, processes and/or methods may be implemented by one or more devices that include logic circuitry. Such a device can be alternately called a computer, and so on. It may be a standalone device or computer, such as a general-purpose computer, or part of a device that has one or more additional functions. In some embodiments, the computer is a specialized computer adapted to and optimally configured for a specific purpose such as for example, providing therapy shocks in emergency situations. The logic circuitry may include a processor and non-transitory computer-readable storage media, such as memories, of the type described in this document. Often, for the sake of convenience, it is preferred to implement and describe a program as various interconnected distinct software modules or features. These, along with data are individually and also collectively referred to herein as software. In some instances, software is combined with hardware, in a mix called firmware.

Various embodiments of methods and algorithms are described below. These methods and algorithms are not necessarily inherently associated with any particular logic device or other apparatus. Rather, they can be advantageously implemented by programs for use by a computing machine, such as a general-purpose computer, a special purpose computer, a microprocessor, a microcontroller, a processor and/or a combination of these devices such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts describe methods in terms of boxes, they also concurrently describe programs.

Figure 9:
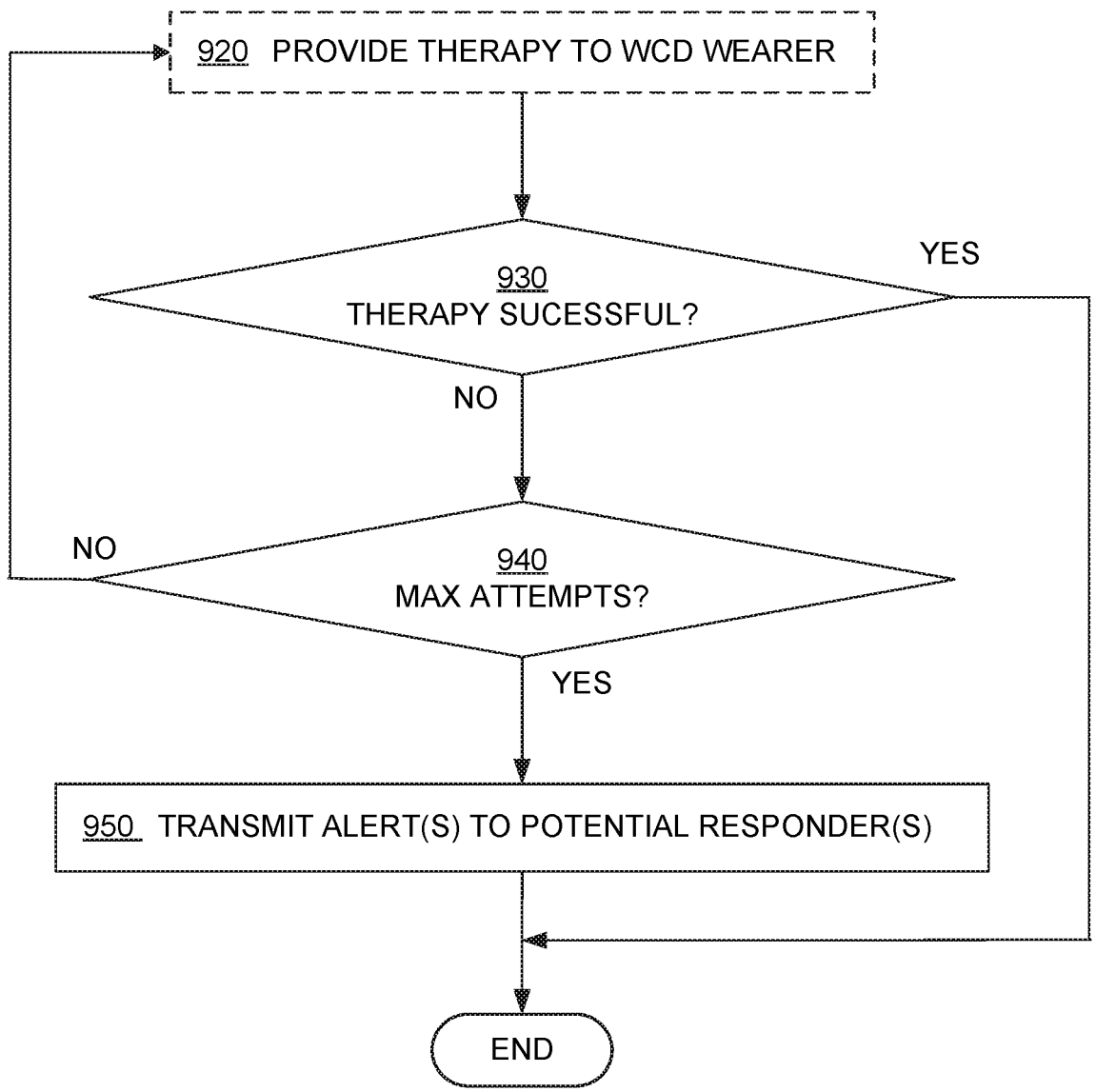
FIG. 9 is a flow diagram illustrating sample methods for use in a WCD system to notify remote responders, according to embodiments.

FIG. 9 is a flow diagram illustrating a notification process 900 for use in a WCD system (such as described above in conjunction with FIGS. 2-8) to notify remote or non-witness responders that the patient requires additional assistance, according to embodiments. Notification process 900, in some embodiments, can start after the WCD system provides a therapy (e.g., a defibrillation shock) to the patient (e.g., patient 182 in FIGS. 2-8) as previously described in conjunction with FIG. 2. While not strictly part of a notification process, the therapy operation is shown as an operation 920 in dashed lines in FIG. 9 to facilitate the description embodiments of notification process 900.

In an operation 930 the patient is monitored to determine whether the therapy was successful. In some embodiments, a processor of the WCD system includes a process or module such as for example, shock success module 370 (FIG.3) configured to determine whether the therapy was successful (e.g., causing the patient's heart to return to a perfusing rhythm). In some embodiments, the therapy is a defibrillation shock and is determined to be successful if the shock caused the patient to no longer experience VF/VT.

If the therapy is successful, notification process 900 ends without sending out a notice that the patient needs additional assistance (e.g., CPR). However, if the therapy is not successful, notification process 900 flows to an operation 940.

In operation 940, it is determined whether the maximum number of unsuccessful therapy attempts has been made. For example, in some embodiments the number of unsuccessful therapy administrations is compared to a maximum number. In some embodiments, the processor of the WCD system includes a process or module such as for example, assistance request module 374 (FIG.3) configured to determine whether the maximum number of unsuccessful therapy administrations (e.g., defibrillation shocks) has been made. According to embodiments, the maximum number is an integer greater than or equal to 1 and is accessible by the processor of the WDC system. For example, in some embodiments the maximum number of unsuccessful therapy administrations is stored in a memory such as memory 338 (FIG. 3) by a user (e.g., patient, physician, clinician or technician, etc.) when the WCD is configured for the patient or at the factory when the WCD system is assembled.

If the number of unsuccessful therapy administrations was not reached, process 900 returns to operation 920 to provide another round of therapy (e.g., another defibrillation shock). In some embodiments, the processor of the WCD system tracks the number of unsuccessful therapy applications. However, if the maximum number was reached, process 900 flows to an operation 950.

In operation 950, a notification or alert is sent or transmitted to potential responders who may be remote from the patient and/or did not witness the patient experiencing the emergency event. In some embodiments, for example, the processor of the WCD system has a process or module the same or similar to notification module 378 (FIG. 3) configured to send or transmit one or more notifications that the patient requires additional assistance. In some embodiments, the WCD system has been configured with the contact information of the potential responders and the notification(s) include information indicating the patient's location and that the patient requires CPR. In some embodiments, a single notification is sent to each of the responders, while in other embodiments the notification is periodically resent. Embodiments of operation 950 are described in more detail below in conjunction with FIGS. 10-15.

Figure 9A:
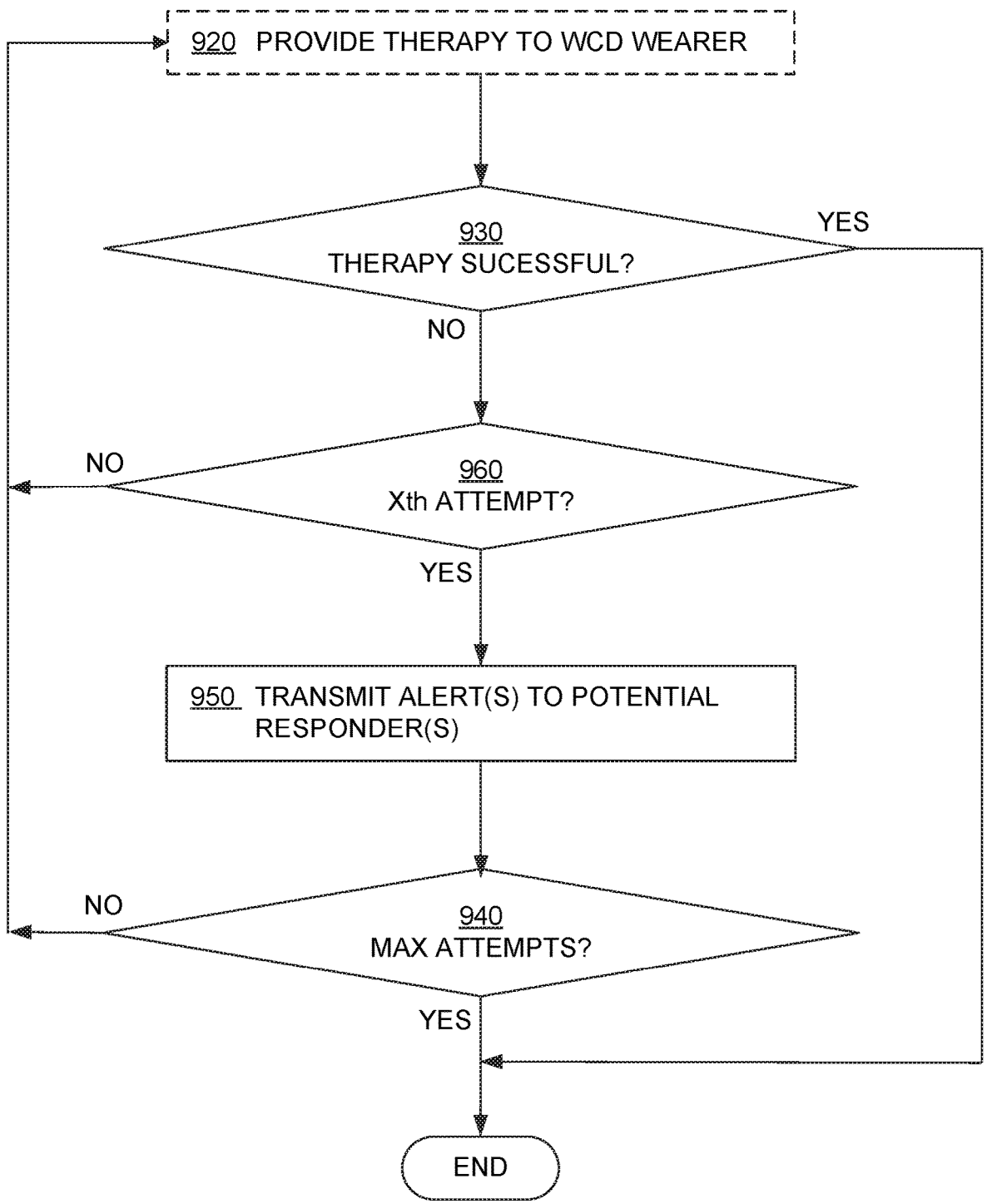
FIG. 9A is a flow diagram illustrating sample methods for use in a WCD system to notify remote responders, according to other embodiments.

FIG. 9A is a flow diagram illustrating a notification process 900A for use in a WCD system (such as described above in conjunction with FIGS. 2-8) to notify remote or non-witness responders that the patient requires additional assistance, according to embodiments. Operations 920, 930, 940, and 950 shown in FIG. 9A are already described above in conjunction with FIG. 9 (in a different order) so will not be described again in detail for notification process 900A.

In operation 920, therapy is provided to the patient and in operation 930 it is determined whether the therapy was successful as previously described according to embodiments. If the therapy was successful, notification process ends without sending out a notice that the patient needs additional assistance (e.g., CPR). However, if the therapy is not successful, in some embodiments notification process 900A flows to an operation 960.

In operation 960, it is determined whether an "Xth" number of unsuccessful therapy attempts have been made. For example, in some embodiments the number of unsuccessful therapy administrations is divided by X, where X is a positive integer, and if there is no remainder it is determined that the therapy attempt was an "Xth" attempt. In some embodiments, the processor of the WCD system includes a process or module such as for example, assistance request module 374 (FIG. 3) configured to determine whether the unsuccessful therapy administration (e.g., defibrillation shocks) was an Xth attempt. For example, operation 960 can implemented to detect every other (i.e., X=2) unsuccessful attempt or every $3^{rd}$ (i.e., X=3) unsuccessful attempt. For example, in some embodiments the Xth number of unsuccessful therapy administrations is stored in a memory such as memory 338 (FIG. 3) by a user (e.g., patient, physician, clinician or technician, etc.) when the WCD is configured for the patient or at the factory when the WCD system is assembled.

If operation 960 determines that the unsuccessful therapy was not an Xth attempt, notification process 900A returns to operation 920. However, if the unsuccessful therapy administration was an Xth attempt, notification process 900A flows to operation 950 and then onto operation 940 (described above in conjunction with FIG. 9).

In some embodiments of notification process 900 (FIG. 9) and notification process 900A in which the WCD system includes a proximity detector as in aforementioned U.S. Pat. No. 9,339,663, operation 950 may be preceded by an operation to detect whether there are bystanders nearby. Responsive to bystanders being detected, the process may in some embodiments proceed to performing a local notification directed to the bystanders instead of performing operation 950. Conversely, responsive to no bystanders being detected, then operation 950 is performed.

Figure 10:
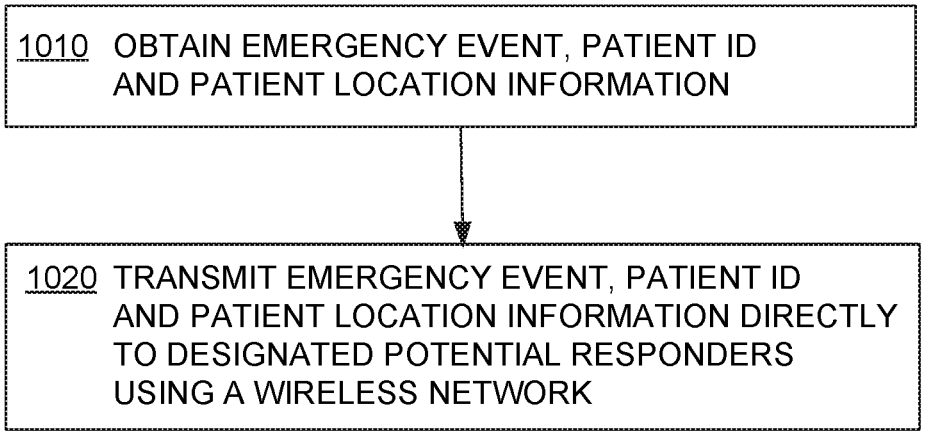
FIG. 10 a flow diagram illustrating sample methods for use in a WCD system for transmitting notifications to remote responders, according to embodiments.

FIG. 10 a flow diagram illustrating an implementation by a WCD system (e.g., as described above in conjunction with FIG. 4) of operation 950 (FIGS. 9 and 9A), according to embodiments. In an operation 1010, the WCD system obtains information related to: the emergency event data (e.g., information related to the unsuccessful therapy); the identification of the patient; and the location of the patient. In some embodiments, the WCD system includes modules and components the same or similar to processor 330, memory 338 and location module 386 (described in conjunction with FIG. 3) configured to obtain this information.

In an operation 1020, the WCD system transmits information including at least some of the emergency event, patient ID and patient location information obtained in operation 1010 to potential responders, using the contact information also obtained in operation 1010. These responders may be remote from the patient and may not have witnessed the emergency event. In some embodiments, the WCD system includes a communication module or component such as communication module 390 (FIG. 3) to transmit the information. In some embodiments, the communication module, the location module, the processor and the memory are part of an external defibrillator of the WCD system, such as external defibrillator 100 (FIG. 4). In some embodiments, the information is transmitted directly from the WCD system to mobile phone number(s) of the responder(s) via SMS messages. In other embodiments, the WCD system may make a wireless phone call to the responder(s) in which the information is in the form of a recorded or synthesized voice message.

Figure 11:
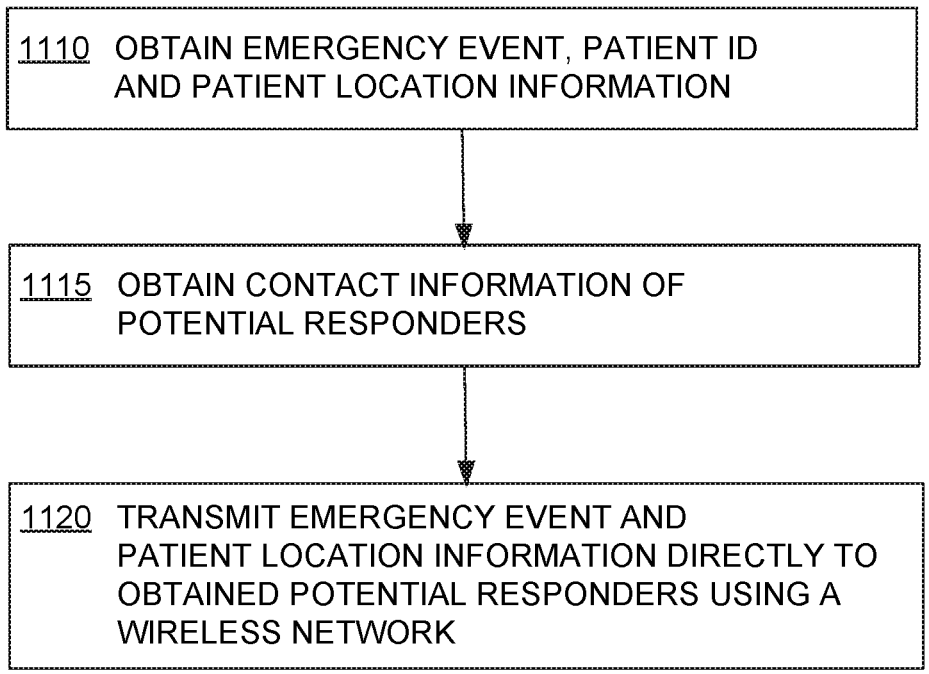
FIG. 11 is a flowchart illustrating sample methods for use in a WCD system for obtaining contact information of and transmitting notifications to remote responders, according to embodiments.

FIG. 11 is a flowchart illustrating an implementation by a WCD system (e.g., as described above in conjunction with FIG. 4) of operation 950 (FIGS. 9 and 9A), according to embodiments. In an operation 1110, the WCD system obtains information related to the emergency event data (e.g., information related to the unsuccessful therapy), the location of the patient, and the identification of the patient. In some embodiments, the WCD system includes modules and components the same or similar to processor 330, location module 386 and memory 338 (described in conjunction with FIG. 3) that are configured to obtain this information. In some embodiments, the location module, processor and memory are disposed in an external defibrillator unit of the WCD system such as external defibrillator 100 (FIG. 5).

In an operation 1115, the WCD system obtains the contact information of the potential responders. In some embodiments, this contact information may be obtained from the memory of an external defibrillator as described above for operation 1110 by a separate mobile communication device such as for example mobile communication device 510 (FIG. 5). In other embodiments, the contact information may be stored in a memory of the mobile communication device itself, or in the WCD server (accessed, for example, by patient ID).

In an operation 1120, the WCD system transmits information including at least some of the information obtained in operation 1110 to potential responders using the contact information obtained in operation 1115. This transmitted information includes enough information for the responder to know the emergency and the patient's location. In some embodiments, the information is transmitted directly from the mobile communication device (described above for operation 1115) to mobile phone number(s) of the responder(s) via SMS messages. In other embodiments, the WCD system may make a wireless phone call to the responder(s) in which the information is included in a recorded or synthesized voice message.

Figure 12:
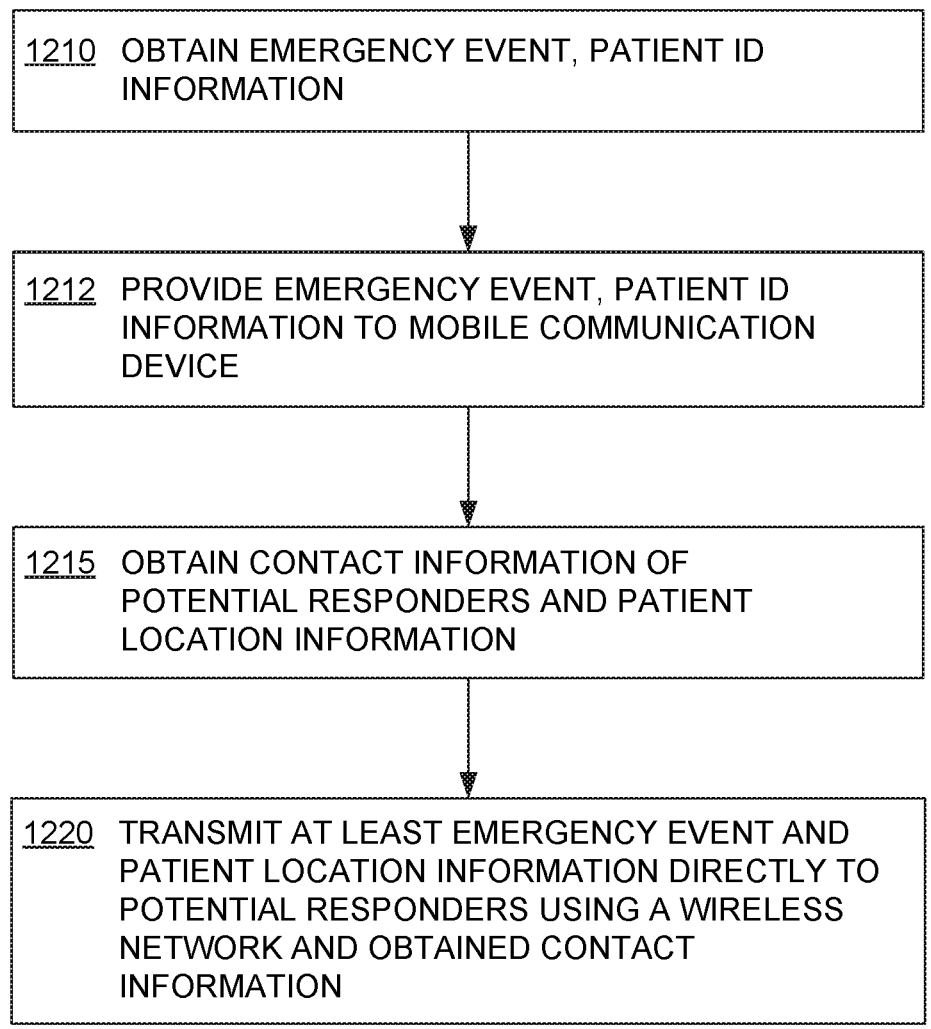
FIG. 12 is a flowchart illustrating sample methods for use in a WCD system, which includes a mobile communication device, for obtaining contact information of and transmitting notifications to remote responders, according to embodiments.

FIG. 12 is a flowchart illustrating an implementation by a WCD system (e.g., as described above in conjunction with FIG. 4) of operation 950 (FIGS. 9 and 9A), according to embodiments. In an operation 1210, the WCD system obtains information related to the emergency event data (e.g., information related to the unsuccessful therapy) and the identification of the patient. In some embodiments, the WCD system includes modules and components the same or similar to processor 330 and memory 338 (described in conjunction with FIG. 3) that are configured to obtain this information. In some embodiments, the processor and memory are disposed in an external defibrillator unit of the WCD system, such as external defibrillator 100 (FIG. 5).

In an operation 1212, the WCD system provides at least some of the information obtained in operation 1110 to a mobile communication device such as mobile communication device 510 (FIG. 5). In some embodiments, the external defibrillator described for operation 1210 provides this information to the mobile communication device.

In an operation 1215, the WCD system obtains the contact information of the potential responders and the location information of the patient. In some embodiments, this contact and patient location information may be obtained from the memory of the external defibrillator described above for operation 1210 by the mobile communication device. In other embodiments, the contact information may be stored in a memory of the mobile communication device itself, or in the WCD server (accessed, for example, by patient ID). Still further, the location information may be obtained by the mobile communication device using a location module (similar to location module 386 of FIG. 3) that is disposed or implemented in the mobile communication device itself.

In an operation 1220, the WCD system transmits information including at least some of the information obtained in operations 1210 and 1215 to potential responders using the contact information obtained in operation 1215. In some embodiments, the information is transmitted directly from the mobile communication device to mobile phone number(s) of the responder(s) via SMS messages. In some embodiments, the information is transmitted via a wireless comlink, wireless service provider network, and communication network such as, for example, remote comlink 572 (FIG. 5), wireless service provider network 580 (FIG. 5) and communication network 480 (FIG. 5). In other embodiments, the WCD system may make a wireless phone call to the responder(s) in which the information is in a recorded or synthesized voice message instead of or in addition to an SMS message.

Figure 13:
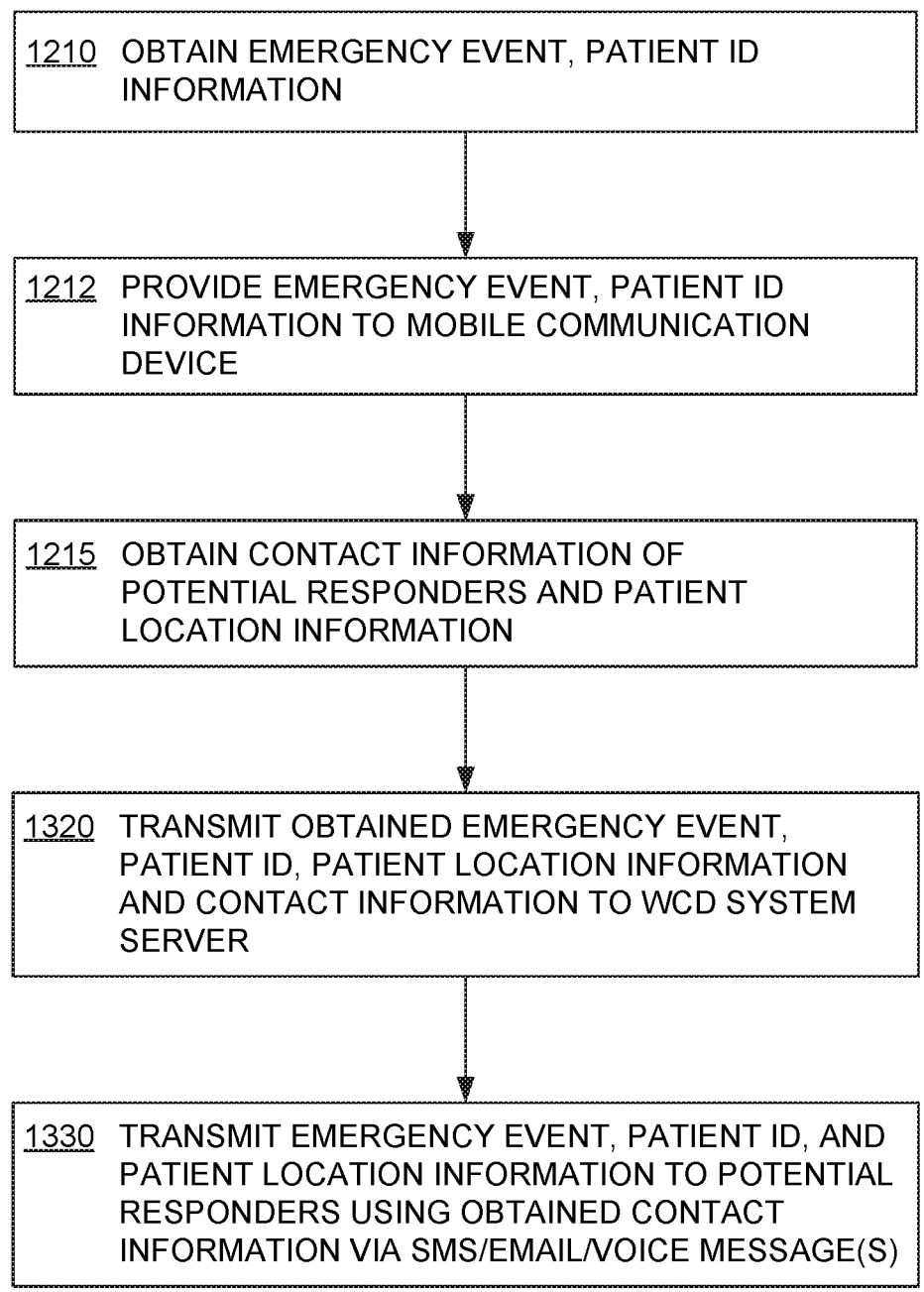
FIG. 13 is a flowchart illustrating sample methods for use in a WCD system, which includes a WCD system server, for transmitting notifications to remote responders, according to embodiments.

FIG. 13 is a flowchart illustrating an implementation by a WCD system (e.g., as described above in conjunction with FIG. 4) of operation 950 (FIGS. 9 and 9A), according to embodiments. The flowchart of FIG. 13 includes operations 1210, 1212, and 1215 as described above in conjunction with FIG. 12. However, after operation 1215 is performed, instead of flowing to operation 1220, in the flowchart of FIG. 13 an operation 1320 is performed.

In operation 1320, the WCD system transmits information including at least some of the information obtained in operations 1210 and 1215 to a WCD system server via a wireless comlink, wireless service provider network, and communication network such as, for example, WCD system server 685 (FIG. 6), remote comlink 572 (FIG. 6), wireless service provider network 580 (FIG. 6) and communication network 480 (FIG. 6).

In an operation 1330 at least some of the information received by the WCD system server in operation 1320 is transmitted by the WCD system server to the responders using the contact information obtained in operation 1320. This transmitted information includes enough information for the responder to know the emergency and the patient's location. In some embodiments, the WCD system server sends this information to mobile phone number(s) of the responder(s) via SMS messages and/or recorded/synthesized voice messages. In some embodiments, the information is transmitted via a wireless service provider network, a remote comlink and/or a wired comlink such as, for example, remote comlink 682 (FIG. 6), wireless service provider network 680 (FIG. 6) and wired comlink 687 (FIG. 6).

Figure 14:
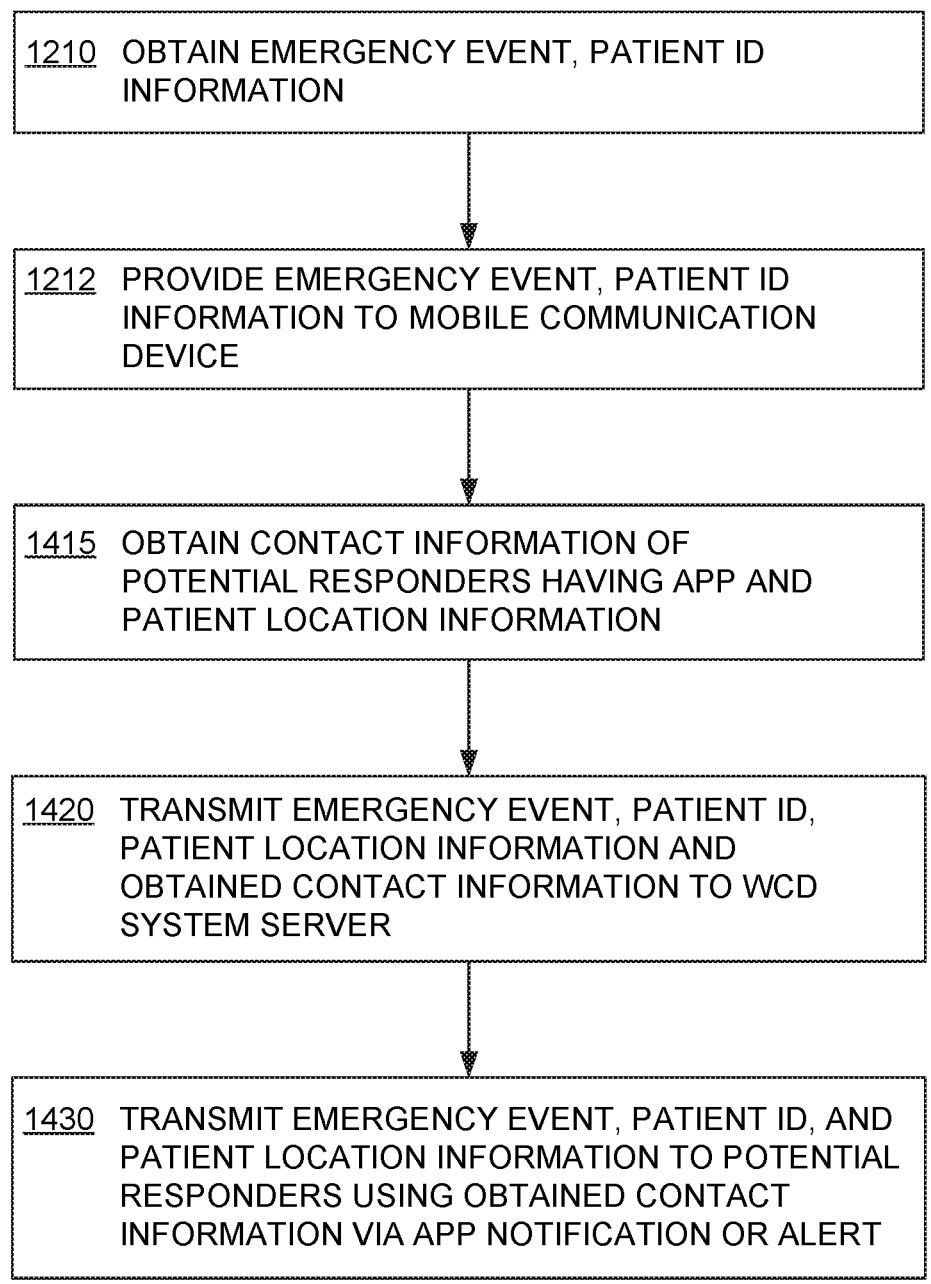
FIG. 14 is a flowchart illustrating sample methods for use in a WCD system, which includes a WCD system server, for transmitting notifications to remote responders via a device configured with a notification app, according to embodiments.

FIG. 14 is a flowchart illustrating an implementation by a WCD system (e.g., as described above in conjunction with FIG. 4) of operation 950 (FIGS. 9 and 9A), according to embodiments. The flowchart of FIG. 14 includes operations 1210 and 1212 as described above in conjunction with FIG. 12. However, after operation 1212 is performed, instead of flowing to operation 1215, in the flowchart of FIG. 14 an operation 1415 is performed.

In operation 1415, the WCD system obtains the contact information of the potential responders and the location information of the patient. In some embodiments, this contact and patient location information may be obtained by the mobile communication device from the memory of the external defibrillator (e.g., external defibrillator 100 of FIG. 7) of the WCD system. In other embodiments, the contact information may be stored in a memory of the mobile communication device itself. Still further, the location information may be obtained by the mobile communication device using a location module (similar to location module 386 of FIG. 3) that is disposed or implemented in the mobile communication device itself.

In some embodiments according to FIG. 14, the contact information for the potential responders is the contact information of responders who have a notification app installed on their receiving devices. For example, these potential responders may have receiving devices such as receiving devices 790 (FIG. 7) in which they have installed a notification app.

In operation 1420, the WCD system transmits information including at least some of the information obtained in operations 1210 and 1415 to a WCD system server via a wireless comlink, wireless service provider network, and communication network such as, for example, WCD system server 685 (FIG. 7), remote comlink 572 (FIG. 7), wireless service provider network 580 (FIG. 7) and communication network 480 (FIG. 7).

In an operation 1430 at least some of the information received by the WCD system server in operation 1420 is transmitted by the WCD system server to the notification app on the responders' receiving devices, using the contact information obtained in operation 1420. This transmitted information includes enough information for the responder to know the emergency and the patient's location. In some embodiments, the WCD system server sends this information to via a wireless service provider network and a remote comlink such as, for example, wireless service provider network 680 and remote comlink 772 as described above in conjunction with FIG. 7.

Figure 15:
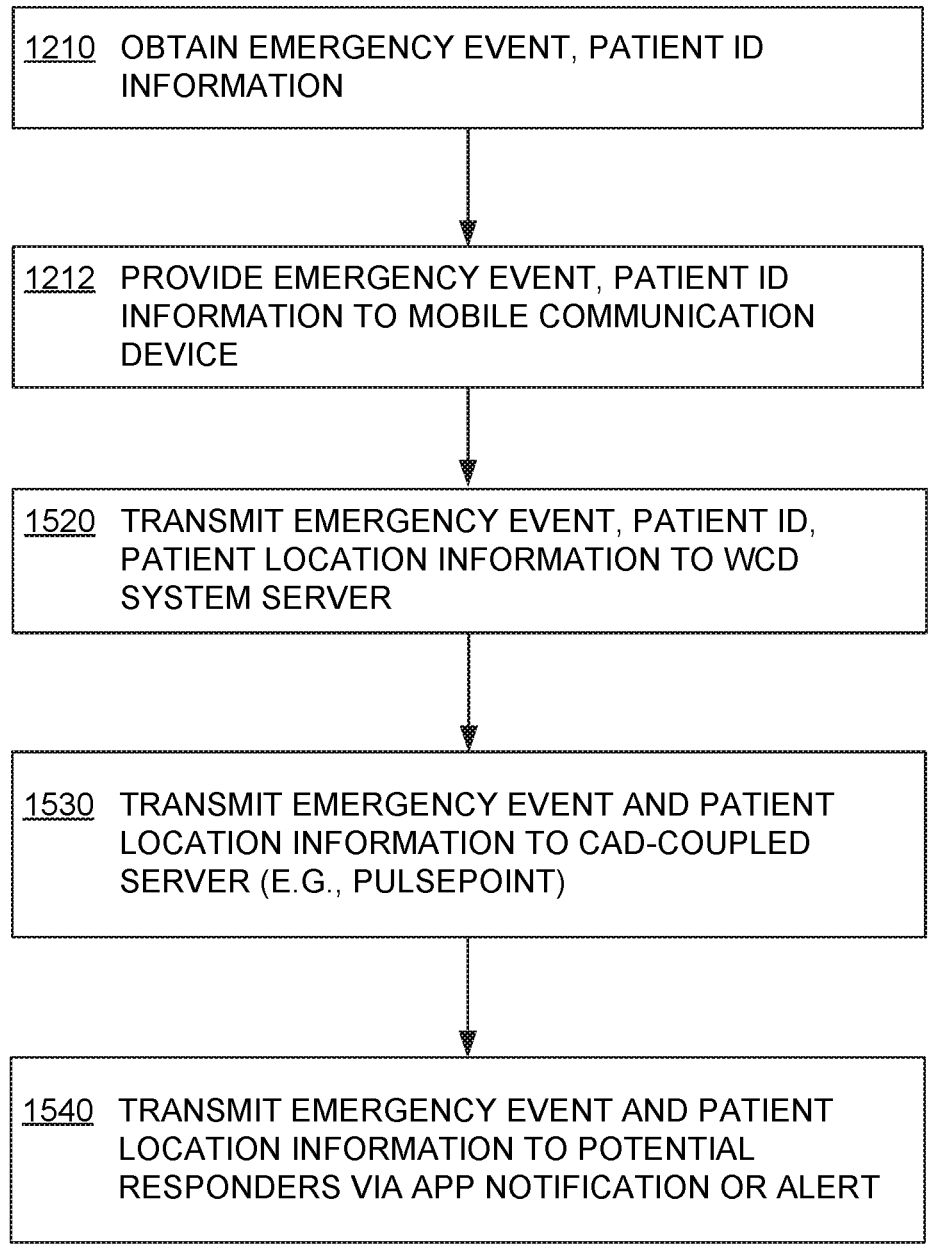
FIG. 15 is a flowchart illustrating sample methods for use in a WCD system, which includes a WCD system server, for transmitting notifications to remote responders via a CAD-coupled server, according to embodiments.

FIG. 15 is a flowchart illustrating an implementation by a WCD system (e.g., as described above in conjunction with FIG. 4) of operation 950 (FIGS. 9 and 9A), according to embodiments. The flowchart of FIG. 15 includes operations 1210 and 1212 as described above in conjunction with FIG. 12. However, after operation 1212 is performed, instead of flowing to operation 1215, in the flowchart of FIG. 15 an operation 1520 is performed.

In operation 1520, the WCD system transmits information including at least some of the information obtained in operations 1210 to a WCD system server via a wireless comlink, wireless service provider network, and communication network such as, for example, WCD system server 685 (FIG. 8), remote comlink 572 (FIG. 8), wireless service provider network 580 (FIG. 8) and communication network 480 (FIG. 8).

In an operation 1530 at least some of the information received by the WCD system server in operation 1520 is transmitted by the WCD system server to a CAD-coupled server such as, for example, CAD-coupled server 885 as described above in conjunction with FIG. 8. In some embodiments, the CAD-coupled server is a PulsePoint server (enhanced to receive/process information from the WCD system server), and the information transmitted to the CAD-coupled server does not include any contact information for potential responders as the PulsePoint server has this information.

In an operation 1540, the CAD-coupled server transmits information to the notification app on the responders' receiving devices. This transmitted information includes enough information for the responder to know the emergency and the patient's location. In some embodiments, the information also includes map information to facilitate the responder in locating the patient, and may include information indicating that an AED is not needed (since the WCD has provided one or more unsuccessful shocks) and omit AED location information which can be included in the CAD-coupled server notifications. In some embodiments, the CAD-coupled server sends this information to via a wireless service provider network and a remote comlink such as, for example, remote comlink 872 as described above in conjunction with FIG. 8. In some embodiments, remote comlink is implemented using a wireless service provider network similar to wireless service network provider 680 (FIG. 6).

Figure 16:
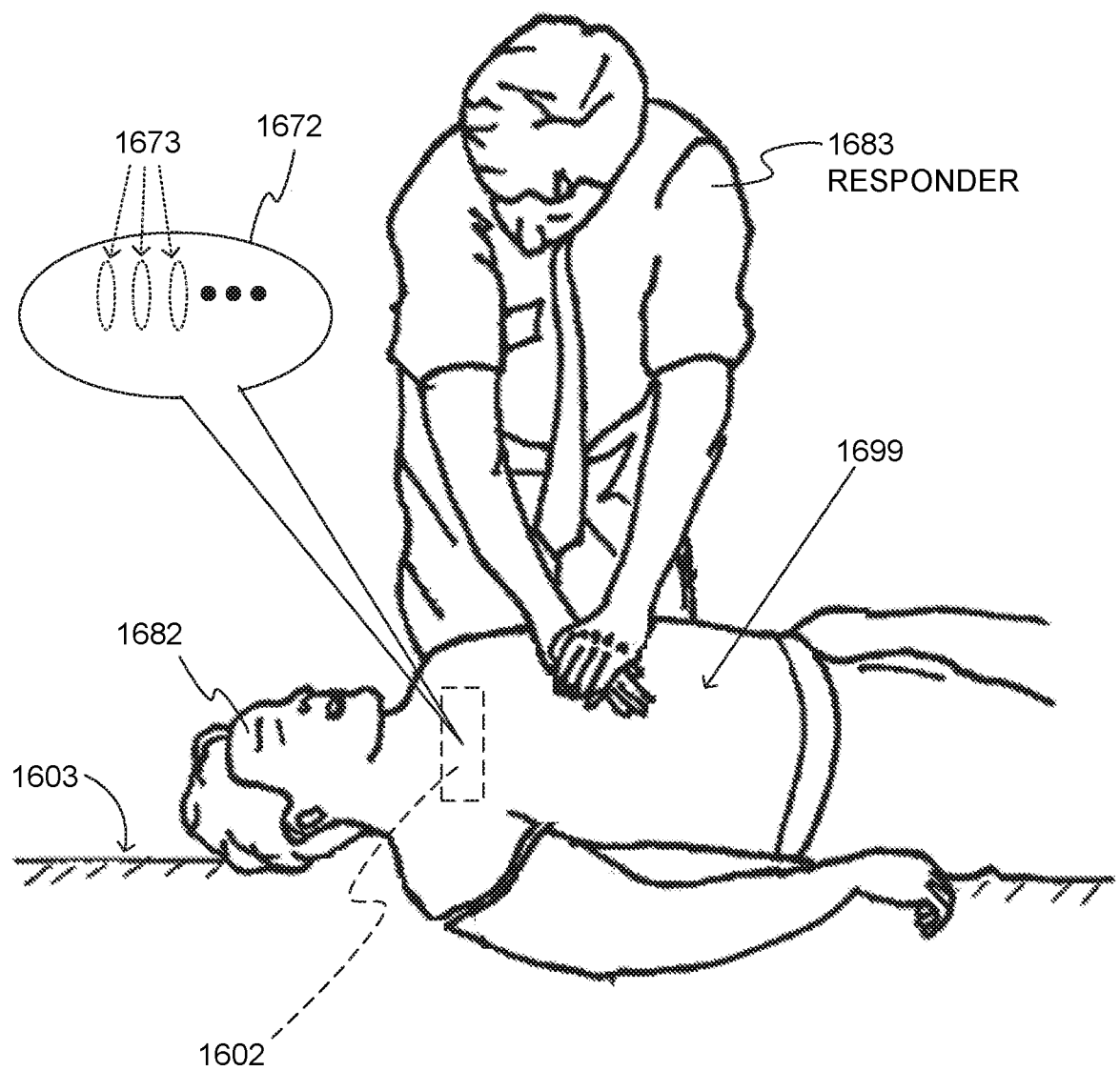
FIG. 16 is a diagram illustrating a sample WCD system configured to assist a respondent in performing CPR after notification, according to embodiments.

FIG. 16 is a diagram of an example scene, where a patient 1682 has fallen on ground 1603, in an emergency. Patient 1682 is wearing an outer garment 1699. Patient 1682 is also wearing a WCD system 1602, of which only a small portion is shown, and in dashed lines, as it is obscured by outer garment 1699. A bystander 1683 has been engaged, and is performing CPR chest compressions on patient 1682. This scene may occur when the WCD system 1602 has delivered the maximum number of shocks to the patient, sent notifications or alerts to remote or non-witness responders, and bystander 1683 is one of the responders who received the notification.

WCD system 1602 may include processor 230 (FIG. 2), support structure 170 (FIG. 1), energy storage module 250 (FIG. 2), and discharge circuit 255 (FIG. 2). It may also have speaker system (not shown) as part of user interface 280 (FIG. 2), which has been configured to output a transmitted sound 1672. In this example, transmitted sound 1672 has substantially periodic contents 1673. Contents 1673 may be designed to assist bystander 1683 to perform CPR chest compressions to patient 1682. For example, contents 1673 may be sequences of tones, to which bystander 1683 can synchronize their sequences of compressions—in other words a metronome-type sound. Transmitted sound 1672 may further communicate a request to not remove the support structure from the patient. In addition, transmitted sound 1672 can further communicate reminders to perform CPR ventilations as part of the overall CPR. Related transmitted sounds, or images, can assure bystander 1683 that no shock is impending, that there will be ample notification well before a shock is prepared, and that shock will not happen before bystander 1683 is ready.

In a number of embodiments of WCD system 1602, CPR chest compressions that are performed on patient 1682 are detected. Detection may be in a number of ways. In some embodiments, WCD system 1602 includes one or more motion detectors 384 (FIG. 3), which can be coupled to the support structure. This way, the performed CPR chest compressions can be detected by the one or more motion detectors 384. Moreover, at least one of motion detectors 384 can be coupled to the support structure at such a point as to be near the sternum of patient 1682, and at least one of motion detectors 384 can be coupled to the support structure at such a point as to be near the back of patient 1682. Alternately or in addition, WCD system 1602 can have an impedance sensing module, for example from measurement circuit 220 (FIG. 2); in such cases, the performed CPR chest compressions can be detected by the impedance sensing module, as the CPR chest compressions affect the patient impedance.

In embodiments of WCD system 1602 where performed CPR chest compressions are detected, feedback may be additionally communicated to the user. The feedback may refer at least to a depth or to a rate of the detected CPR chest compressions. The feedback can be communicated in a number of ways. For example, in some embodiments the feedback is communicated by transmitted sound 1672. In other embodiments, the feedback is communicated by visual representations on screen 375 on WCD system 1602.

In some embodiments, the detected CPR chest compressions are recorded, along with other events. The detected CPR chest compressions may be analyzed, Figures of Merit may be computed, and so on. It should be remembered that, unless more is known, bystander 1683 is likely not a trained first responder, but a well-meaning "Good Samaritan" who may have even learned First Aid and CPR, but many years prior and may have forgotten some of it.

In some embodiments, WCD system 1602 makes further provisions for shocking the patient after CPR is received. Accordingly, transmitted sound 1672 may further communicate a request for bystander 1683 to no longer touch patient 1682. This request may be communicated after at least two minutes of detecting chest compressions, in which case it may be judged that patient 1682 has received some benefit from the CPR. In some embodiments, the request to no longer touch the patient can be communicated less than two minutes after detecting the chest compressions, for example in cases where it is judged that the CPR is poor, and not improving despite any prompts or feedback.

The request to not touch the patient may be communicated anyway as a safety feature, even if bystander 1983 has not yet touched patient 1682. It could be that no bystander gave CPR, but someone was preparing to do so.

In some embodiments, additional provisions for shocking the patient after CPR can include that transmitted sound 1672 further communicates a request to say one or more preset affirmative words, such as "CLEAR", "YES", or "ALL CLEAR". It may be possible to be able to detect reliably every time whether bystander 1683 is no longer touching patient 1682, but engaging bystander 1683 this way may also help. In some of these embodiments, WCD system 1602 further includes microphone (not shown) as part of user interface 280 (FIG. 2) coupled to the support structure. This microphone can be configured to sense an ambient sound, and the electrical charge can be discharged through the patient responsive to the sensed ambient sound including one or more of the preset affirmative words.

In the methods described above, each operation can be performed as an affirmative step of doing, or causing to happen, what is written that can take place. Such doing or causing to happen can be by the entire system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily the present invention. Plus, any reference to any prior art in this description is not, and should not be taken as, an acknowledgement or any form of suggestion that this prior art forms parts of the common general knowledge in any country.

This description includes one or more examples, but that does not limit how the invention may be practiced. Indeed, examples or embodiments of the invention may be practiced according to what is described, or yet differently, and also in conjunction with other present or future technologies. Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, a phrase in the form of "A and/or B" is used to indicate "A or B or both A and B". Further, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in any number of ways, as will be apparent to a person skilled in the art after reviewing the present disclosure, beyond any examples shown in this document.

The following claims define certain combinations and subcombinations of elements, features and steps or operations, which are regarded as novel and non-obvious. Additional claims for other such combinations and subcombinations may be presented in this or a related document.

The embodiments of the invention in which an exclusive property or privilege is claimed are defined as follows:

1. A wearable cardioverter defibrillator (WCD) system, comprising:
a support structure configured to be worn by a patient;
a plurality of electrodes coupled to or integrated in the support structure;
an energy storage module configured to store an electrical charge;
a discharge circuit configured to be coupled to the energy storage module and configured to deliver one or more shocks to the patient while the support structure is worn by the patient using the plurality of electrodes and electrical charge stored in the energy storage module;
a location module configured to determine a location of the patient;
a proximity detector configured to detect when one or more bystander(s) are near the patient;
an assistance request module coupled to the proximity detector, wherein:
the assistance request module is configured to determine that one or more responder(s) should be notified that the patient requires further assistance when the proximity detector detects that the one or more bystander(s) are not near the patient, and
the assistance request module is configured to determine that the one or more responder(s) need not be notified that the patient requires further assistance when the proximity detector detects that the one or more bystander(s) are near the patient;
a notification module, coupled to the assistance request module, configured to obtain information comprising emergency event information, patient identification information, patient location information, and responder contact information in response to a determination that the one or more responder(s) should be notified that the patient requires further assistance; and
a communication module, coupled to the notification module, configured to transmit at least some of the information obtained by the notification module.

2. The WCD system of claim 1, further comprising a processor configured to be coupled to the support structure and to implement at least a part of the location module and/or the communication module.

3. The WCD system of claim 2, further comprising a mobile communication device, separate from the processor, communicatively coupled to the processor and to implement at least another part of the location module and/or the communication module.

4. The WCD system of claim 3, wherein the processor is configured to transmit the emergency event information and the patient identification information to the mobile communication device.

5. The WCD system of claim 1, wherein the communication module is configured to transmit the at least some information obtained from the notification module in a voice message or a SMS message or both the voice message and the SMS message to the one or more responder(s) using contact information stored in the WCD system.

6. The WCD system of claim 1, wherein the communication module is configured to transmit the at least some information obtained from the notification module to a WCD system server configured to communicate the at least some information to the one or more responders using contact information stored in the WCD system.

7. The WCD system of claim 6, wherein the WCD system server is configured to communicate the at least some information obtained from the notification module to the one or more responder(s) using one or more notification applications configured on one or more device(s) of the one or more responder(s).

8. The WCD system of claim 1, wherein the at least some information, obtained from the notification module, transmitted by the communication module includes an indication that the patient requires cardiopulmonary resuscitation (CPR).

* * * * *